US012757631B2

(12) United States Patent
Saykin et al.

(10) Patent No.: US 12,757,631 B2
(45) Date of Patent: Oct. 6, 2026

(54) PYRAZOLE COMPOUNDS FOR ORGANIC LIGHT EMITTING DIODES AND OTHER APPLICATIONS

(71) Applicant: Kebotix, Inc., Cambridge, MA (US)

(72) Inventors: Semion Saykin, Arlington, MA (US); Victoria Campbell, Somerville, MA (US); Selma Duhovic, Denver, CO (US); David Lee Wheeler, Brighton, MA (US); Kevin Ryan, Watertown, MA (US); Sreeletha Joby Eldo, Andover, MA (US); Nathan Darrell Peterson Ricke, Medford, MA (US); Zhongwei Hu, Newton Upper Falls, MA (US); Dennis Sheberla, Bedford, MA (US); Jhaylen McDavid, Cambridge, MA (US)

(73) Assignee: Kebotix, Inc., Cambridge, MA (US)

( * ) Notice: Subject to any disclaimer, the term of this patent is extended or adjusted under 35 U.S.C. 154(b) by 502 days.

(21) Appl. No.: 18/347,714

(22) Filed: Jul. 6, 2023

(65) Prior Publication Data

US 2024/0016056 A1 Jan. 11, 2024
US 2026/0052901 A9 Feb. 19, 2026

Related U.S. Application Data

(60) Provisional application No. 63/359,290, filed on Jul. 8, 2022.

(51) Int. Cl.
*H10K 85/60* (2023.01)
*C07D 231/22* (2006.01)
(Continued)

(52) U.S. Cl.
CPC ......... *H10K 85/654* (2023.02); *C07D 231/22* (2013.01); *C09K 11/06* (2013.01); *C09K 2211/1018* (2013.01); *H10K 50/11* (2023.02)

(58) Field of Classification Search
None
See application file for complete search history.

(56) References Cited

U.S. PATENT DOCUMENTS 3,172,862 A 3/1965 Gurnee et al.
4,356,429 A 10/1982 Tang
(Continued)

FOREIGN PATENT DOCUMENTS

CN 101682002 B 3/2010
WO WO 90/13148 A1 11/1990
WO WO 2012/116242 A1 8/2012

OTHER PUBLICATIONS

Stephen R. Heller et al. "The IUPAC International Chemical Identifier (InChI)", Chemistry International, Jan.-Feb. 2009, p. 7-9, https://iupac.org/wp-content/uploads/2016/03/chemistry-International-Vol-31-No.1-Jan-Feb-2009-p.-7.pdf (Year: 2009).*
(Continued)

*Primary Examiner* — Seokmin Jeon
(74) *Attorney, Agent, or Firm* — Wolf, Greenfield & Sacks, P.C.

(57) ABSTRACT

The present disclosure generally relates to emitting organic molecules, including but not limited to, pyrazoles such as 2-phenyl-2H-pyrazol-3-yl acetate, etc. In some cases, the molecules are able to emit in blue or green wavelengths. In some aspects, such molecules may be used in organic light emitting diodes. In certain embodiments, the molecules may comprise one or more bridge moieties and one or more chromophores. In some embodiments, these molecules can be used as electroluminescent media in devices requiring light emission as a function of applied voltage. Other
(Continued)

embodiments of the disclosure are generally directed to systems and devices using such molecules, methods of using such molecules, e.g., to control the emission of light, kits involving such molecules, or the like.

19 Claims, 17 Drawing Sheets

(51) Int. Cl.
*C09K 11/06* (2006.01)
*H10K 50/11* (2023.01)

(56) References Cited

U.S. PATENT DOCUMENTS

| | | | | |
|---|---|---|---|---|
| 5,141,671 | A | 8/1992 | Bryan et al. | |
| 5,150,006 | A | 9/1992 | Van Slyke et al. | |
| 7,250,512 | B2 | 7/2007 | Lecloux et al. | |
| 2003/0068535 | A1 | 4/2003 | Takiguchi et al. | |
| 2003/0198831 | A1 | 10/2003 | Oshiyama et al. | |
| 2008/0284318 | A1 | 11/2008 | Deaton et al. | |
| 2010/0243959 | A1* | 9/2010 | Nomura | 252/301.16 |
| 2013/0082908 | A1* | 4/2013 | Lynch | 245/76 |
| 2015/0338563 | A1* | 11/2015 | Kiuchi | G02B 5/3083 |

OTHER PUBLICATIONS

Rajashree Banerjee et al. "Revival of the nearly extinct fluorescence of coumarin 6 in water and complete transfer of energy to rhodamine 123", Soft Matter, 2017, vol. 13, p. 5506-5508 (Year: 2017).*

Borowiecki et al., Synthesis of novel proxyphylline derivatives with dual Anti-Candida albicans and anticancer activity. Eur J Med Chem. Apr. 25, 2018;150:307-333. doi: 10.1016/j.ejmech.2018.02.077. Epub Feb. 27, 2018.

Szilagyi et al., Influence of loperamide on lactose handling and oral-caecal transit time. Aliment Pharmacol Ther. Oct. 1996;10(5):765-70.

Willy et al., Rapid one-pot, four-step synthesis of highly fluorescent 1,3,4,5-tetrasubstituted pyrazoles. Org Lett. Apr. 15, 2011;13(8):2082-5. doi: 10.1021/ol2004947. Epub Mar. 18, 2011.

Xie et al., CuI/L-proline-catalyzed coupling reactions of aryl halides with activated methylene compounds. Org Lett. Oct. 13, 2005;7(21):4693-5.

Desroses et al., A convenient microwave-assisted propylphosphonic anhydride (T3P®) mediated one-pot pyrazolone synthesis. Eur J Org Chem. 2013; 26: 5879-85.

Tigreros et al., Recent progress in chemosensors based on pyrazole derivatives. RSC Adv. May 22, 2020;10(33):19693-19712.

* cited by examiner

COMPOUND 1

3-[3-(Dimethylamino)phenyl]-1-(4-fluorophenyl)-4-(4-{[4-(trifluoromethyl)benzoyl]amino}phenyl)-1H-pyrazol-5-yl acetate FIG. 5A
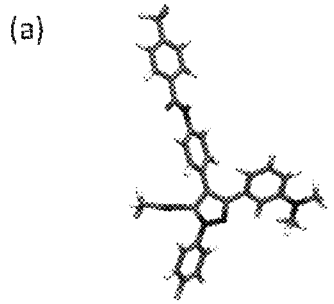
FIG. 5C
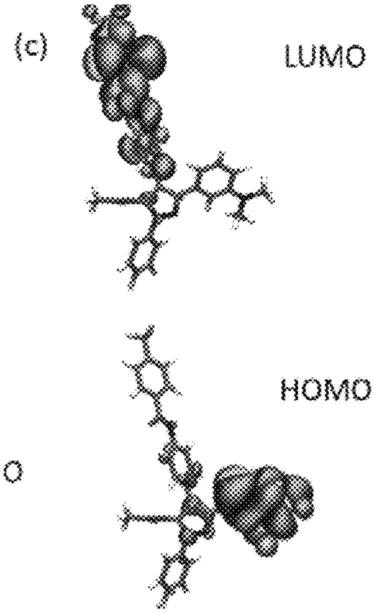
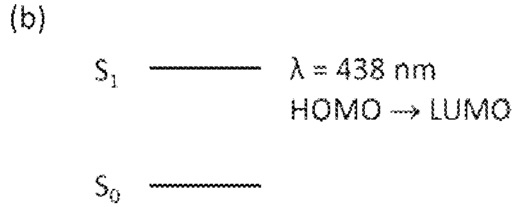
FIG. 5B

APZHDSPLWXDLRC-UHFFFAOYNA-N

BCQZLPBUBKOZSS-UHFFFAOYNA-N

BOMJTHPUDZEPFB-UHFFFAOYNA-N

BRLAZTLRRIOAOZ-UHFFFAOYNA-N

CBPFHHWSAJJJMX-UHFFFAOYNA-N

CHEYCWWQWYEBQT-UHFFFAOYNA-N

CRFIXVVATQXIEV-UHFFFAOYNA-N

FIEGOAADWNCJCD-UHFFFAOYNA-N

GHIQFVANXNJLPR-UHFFFAOYNA-N

BSWVWMPHYWLLNN-UHFFFAOYNA-N

JVRQZQSRHZLZLE-UHFFFAOYNA-N

VMPBRFLTECRQTH-UHFFFAOYNA-N

OEHGGSRMAGICMX-UHFFFAOYNA-N

ULGUGWUFDBIWPQ-UHFFFAOYNA-N

GRPCOGYZIYQJMS-UHFFFAOYNA-N

IMTVACKMXORUMK-UHFFFAOYNA-N

FNDPOTBQLIXHEP-UHFFFAOYNA-N

PAAWKNCADSXJKY-UHFFFAOYNA-N

RHANDXLEIFMQDD-UHFFFAOYNA-N

FOHPQOMVHDSCMT-UHFFFAOYNA-N

UUANYPXXPDKMPJ-UHFFFAOYNA-N

DIHZIJAQHCISIC-UHFFFAOYNA-N

PDUNUPFPWDSZRJ-UHFFFAOYNA-N

VPGQRNDVIATCEN-UHFFFAOYNA-N

JTKYHXJLZLTZBJ-UHFFFAOYNA-N

CCBZVBVEYZIKPI-UHFFFAOYNA-N

FCHZPVWGTHKKOI-UHFFFAOYNA-N

QOMUCQPTIZNUDB-UHFFFAOYNA-N

QYWGODWKDIOGSX-UHFFFAOYNA-N

RDPVXNNXWKUWQS-UHFFFAOYNA-N

QREZGANIQDOWPI-UHFFFAOYNA-N

QUMHWKYPWYMGBY-UHFFFAOYNA-N

CBPYKIAOKVDWPX-UHFFFAOYNA-N

QJAVRZSCHRLIGJ-UHFFFAOYNA-N

ASPDIKWAJQMRCO-UHFFFAOYNA-N

PTFVRTBWIQENON-UHFFFAOYNA-N

QFADIYUJRJQQQU-UHFFFAOYNA-N

JMLOPPZVXIPGMZ-UHFFFAOYNA-N

FGFOKIJGPGXCDY-UHFFFAOYNA-N

HZLLSBCCAOWIHL-UHFFFAOYNA-N

JXWVABYSSASQKD-UHFFFAOYNA-N

JPAHDUTVXPSCFW-UHFFFAOYNA-N

FZNGREDDVGPBIU-UHFFFAOYNA-N

JTKNLTCFAXZGRV-UHFFFAOYNA-N

KMNSNJABLNOBKL-UHFFFAOYNA-N

FKSCQYSGRJKMNI-UHFFFAOYNA-N

UXFQPYLBIFYNAO-UHFFFAOYNA-N

ZGDVSKJMYTYDFX-UHFFFAOYNA-N

ZUWBHFRFDLIBCO-UHFFFAOYNA-N

CLGPRTCGCHMHAE-UHFFFAOYNA-N

CZNYNGWGBPMEHI-UHFFFAOYNA-N

CBWWWVHAABHNJY-UHFFFAOYNA-N

UXBZJIBRXGLLNC-UHFFFAOYNA-N

ZWLYCIXGEUTVQL-UHFFFAOYNA-N

LYHASAIOOPIPST-UHFFFAOYNA-N

RZGPWCGZPUHNBV-UHFFFAOYNA-N

WCNNNVCWRYESKA-UHFFFAOYNA-N

WQOSMTXLFOUJTB-UHFFFAOYNA-N

WXIQEEANSYMJCV-UHFFFAOYNA-N

XAAWXWUCWPKXGQ-UHFFFAOYNA-N

XZSXEQWJFCGXEP-UHFFFAOYNA-N

YADNZLJAJJQOFY-UHFFFAOYNA-N

ZOOFJHDVTYSMSM-UHFFFAOYNA-N

ZTTTYNBVNKTWMC-UHFFFAOYNA-N

RJSBRNWTAKKUNE-UHFFFAOYNA-N

UAKJOPZBFONQFS-UHFFFAOYNA-N

UECNXZHCOOYLCZ-UHFFFAOYNA-N

UEHNABXWZLQDEB-UHFFFAOYNA-N

UQFGCCANRNGVSM-UHFFFAOYNA-N

UWKGBUFCOLUTMS-UHFFFAOYNA-N

VATARVYRYVYZOH-UHFFFAOYNA-N

VJVXKLZBPZLKIQ-UHFFFAOYNA-N

POHKARBWLJRQMP-UHFFFAOYNA-N

PSYZKNGUTMLXIX-UHFFFAOYNA-N

QAWFUVBQPBMUBP-UHFFFAOYNA-N

QKAAVGQNNXKEOI-UHFFFAOYNA-N

QPCMZRPNBGHOHH-UHFFFAOYNA-N

QQJOWIRVQFJHTG-UHFFFAOYNA-N

QRKBEUXOLZDZIS-UHFFFAOYNA-N

QXOVYVVNXGNNPY-UHFFFAOYNA-N

JMXAHDFYVDFKGH-UHFFFAOYNA-N

KNJVRORCBOYOFD-UHFFFAOYNA-N

KQYWRHGRGRYRGF-UHFFFAOYNA-N

KXWIDJGUUYJZQO-UHFFFAOYNA-N

LBJNDXHNXHOIOW-UHFFFAOYNA-N

LNKUDJQQOLKMFV-UHFFFAOYNA-N

NEAKQGPMRGSYKG-UHFFFAOYNA-N

PJZMUZZOUTWQLC-UHFFFAOYNA-N

FOHZCHCZAPFGNM-UHFFFAOYNA-N

GJRJWVFKNPZMFH-UHFFFAOYNA-N

GVZRPOATSVSGAJ-UHFFFAOYNA-N

HLYMCAWWPYGENR-UHFFFAOYNA-N

HNADRWIHKQBHPA-UHFFFAOYNA-N

IAZQZQPAGWVXQI-UHFFFAOYNA-N

IPUBYXNOXMHRIQ-UHFFFAOYNA-N

ITSAWPYMAXGGTC-UHFFFAOYNA-N

UWDUNMFSWRVPRD-UHFFFAOYNA-N

OZKHDDPBPHPAHD-UHFFFAOYNA-N

YUXQXEOZJBDVCV-UHFFFAOYNA-N

PYRAZOLE COMPOUNDS FOR ORGANIC LIGHT EMITTING DIODES AND OTHER APPLICATIONS

RELATED APPLICATIONS

This application claims the benefit under 35 U.S.C. § 119(e) of U.S. Provisional Application Ser. No. 63/359,290, filed on Jul. 8, 2022, entitled "Pyrazole Compounds for Organic Light Emitting Diodes and Other Applications," which is incorporated herein by reference in its entirety.

GOVERNMENT FUNDING

This invention was made with government support under Grant. No. DE-SC0020762 awarded by the Department of Energy. The government has certain rights in the invention.

FIELD

The present disclosure generally relates to emitting organic molecules, including but not limited to, pyrazoles such 2-phenyl-2H-pyrazol-3-yl acetate compounds, etc. In some cases, the molecules are able to be excited by electric potential and may emit light in the visible spectrum.

BACKGROUND

Organic light-emitting diode (OLED) are light-emitting diodes (LED) in which an organic compound is placed between two conductors and shows electroluminescence in response to an excitation such as an electric current. For example, when a voltage is applied, an OLED material may emit light of a given wavelength. Such materials may be used in a variety of applications such as displays for televisions, computer screens, and smart phones; in solid-state lighting such as outdoor or indoor luminaires, or automotive luminaires, as well as in smart labels and wearable devices. However, as many OLED materials exhibit limited spectral ranges and stability, there remains a need for new types of OLED materials for various applications. This point is particularly true for blue electroluminescent compounds due to their intrinsically low electrochemical stability.

OLED materials typically work through the recombination of electrons and holes in a host transport material that cause radiative decay of the molecular excited levels. This excitation results in interactions between electrons and holes that splits the energy levels into dark triplets and bright singlets.

Conventional OLEDs have a maximum theoretical efficiency of 25% due to the recombination of electrons and holes that affords a statistical mixture of four spin states (one singlet and three triplet sublevels). OLED material design has primarily focused on finding ways to harvest the energy of the dark triplet states into usable emissive states. However, colors such as blue, violet, and cyan require higher energy excited states that facilitated the degradation process of the OLED. Accordingly, improvements are needed.

SUMMARY

The present disclosure generally relates to emitting organic molecules, including but not limited to, pyrazoles such as 2-phenyl-2H-pyrazol-3-yl acetate compounds, etc. In some cases, the molecules are able to be excited by electric potential and may emit light in the visible and ultraviolet (UV) spectrum. The subject matter of the present disclosure involves, in some cases, interrelated products, alternative solutions to a particular problem, and/or a plurality of different uses of one or more systems and/or articles.

Certain embodiments are generally directed to certain classes of emitting organic molecules that can be used in OLEDs (organic light-emitting diodes) or other applications. These include certain classes of pyrazole-bridged molecules. For example, some embodiments provide systems and methods for preparing blue OLEDs.

In some embodiments, the organic molecules comprise two or more chromophores bridged by a pyrazole moiety at two or three of the carbon positions. The "bridge" generally refers to a molecular fragment that may be pi (π)-conjugated, and can be covalently linked between two or more chromophore moieties. The chromophore moieties may include a "donor" fragment that is likely to donate electron from its highest occupied molecular orbital (HOMO), and an "acceptor" fragment that is likely accept electron in its lowest unoccupied molecular orbital (LUMO). Without wishing to be bound by any theory, it is believed that the bridge moiety can enhance fluorescence from the molecule, may impart steric rigidity to the molecule, and/or may restrict the chromophores moieties (e.g., the donor and acceptor moieties) into specific configurations. This restriction, in turn, may lead to delocalization of electronic states in the linked chromophores, and/or may prevent the overlap between the conjugated pi (π) system of the chromophore moieties. Examples of suitable bridge molecules include, but are not limited to, phenyl, biphenyl, 2,7-fluorenyl-, 3,6-(9(H)-carbazoyl), 1,3,5-triazinyl-, furyl, thienyl, pyridyl and others.

In addition, in some embodiments, the organic molecules may be electroluminescent. In some cases, the organic molecules can be compatible with vapor-deposition and/or solution-processed OLED technologies.

One aspect is generally drawn to an electroluminescent device. In one set of embodiments, the electroluminescent device comprises an electroluminescent region comprising a pyrazole, and a voltage source able to apply voltage to the electroluminescent region. In another set of embodiments, the electroluminescent device comprises a cathode, an anode, a voltage source electrically connecting the anode and the cathode, and an electroluminescent region comprising a 1,2-pyrazole, positioned between cathode and anode.

Another aspect is generally drawn to a molecule. In some embodiments, the molecule is selected from the group consisting of the following molecules, each identified by a first hash block of an InChIKey representation of the molecule:

APZHDSPLWXDLRC,

BCQZLPBUBKOZSS,

BOMJTHPUDZEPFB,

BRLAZTLRRIOAOZ,

CBPFHHWSAJJJMX,

CHEYCWWQWYEBQT,

CRFIXVVATQXIEV,

FIEGOAADWNCJCD,

FOHZCHCZAPFGNM,

-continued

GJRJWVFKNPZMFH,

GVZRPOATSVSGAJ,

HLYMCAWWPYGENR,

HNADRWIHKQBHPA,

IAZQZQPAGWVXQI,

IPUBYXNOXMHRIQ,

ITSAWPYMAXGGTC,

JMXAHDFYVDFKGH,

KNJVRORCBOYOFD,

KQYWRHGRGRYRGF,

KXWIDJGUUYJZQO,

LBJNDXHNXHOIOW,

LNKUDJQQOLKMFV,

NEAKQGPMRGSYKG,

PJZMUZZOUTWQLC,

POHKARBWLJRQMP,

PSYZKNGUTMLXIX,

QAWFUVBQPBMUBP,

QKAAVGONNXKEOI,

QPCMZRPNBGHOHH,

QQJOWIRVQFJHTG,

QRKBEUXOLZDZIS,

QXOVYVVNXGNNPY,

RJSBRNWTAKKUNE,

UAKJOPZBFONQFS,

UECNXZHCOOYLCZ,

UEHNABXWZLQDEB,

UQFGCCANRNGVSM,

UWKGBUFCOLUTMS,

VATARVYRYVYZOH,

VJVXKLZBPZLKIQ,

WCNNNVCWRYESKA,

WQOSMTXLFOUJTB,

WXIQEEANSYMJCV,

XAAWXWUCWPKXGQ,

XZSXEQWJFCGXEP,

YADNZLJAJJQOFY,

ZOOFJHDVTYSMSM,

ZTTTYNBVNKTWMC,

ZUWBHFRFDLIBCO,

-continued

CLGPRTCGCHMHAE,

CZNYNGWGBPMEHI,

CBWWWVHAABHNJY,

UXBZJIBRXGLLNC,

ZWLYCIXGEUTVQL,

LYHASAIOOPIPST,

RZGPWCGZPUHNBV,

JXWVABYSSASQKD,

JPAHDUTVXPSCFW,

FZNGREDDVGPBIU,

JTKNLTCFAXZGRV,

KMNSNJABLNOBKL,

FKSCQYSGRJKMNI,

UXFQPYLBIFYNAO,

ZGDVSKJMYTYDFX,

CBPYKIAOKVDWPX,

QJAVRZSCHRLIGJ,

ASPDIKWAJQMRCO,

PTFVRTBWIQENON,

QFADIYUJRJQQQU,

JMLOPPZVXIPGMZ,

FGFOKIJGPGXCDY,

HZLLSBCCAOWIHL,

JTKYHXJLZLTZBJ,

CCBZVBVEYZIKPI,

FCHZPVWGTHKKOI,

QOMUCQPTIZNUDB,

QYWGODWKDIOGSX,

RDPVXNNXWKUWQS,

QREZGANIQDOWPI,

QUMHWKYPWYMGBY,

FNDPOTBQLIXHEP,

PAAWKNCADSXJKY,

RHANDXLEIFMQDD,

FOHPQOMVHDSCMT,

UUANYPXXPDKMPJ,

DIHZIJAQHCISIC,

PDUNUPFPWDSZRJ,

VPGQRNDVIATCEN,

GHIQFVANXNJLPR,

BSWVWMPHYWLLNN,

-continued

JVRQZQSRHZLZLE,

VMPBRFLTECRQTH,

OEHGGSRMAGICMX,

ULGUGWUFDBIWPQ,

GRPCOGYZIYQJMS,

IMTVACKMXORUMK,

UWDUNMFSWRVPRD,

OZKHDDPBPHPAHD,

YUXQXEOZJBDVCV.

Yet another aspect is drawn to a method. In one set of embodiments, the methods comprises applying voltage to an electroluminescent material comprising a pyrazole to cause the electroluminescent material to exhibit light emission. In another set of embodiments, the method comprises applying voltage to an electroluminescent material comprising a molecule selected from FIGS. 7-19 to cause the electroluminescent material to emit light.

In still another set of embodiments, the method comprises applying voltage to an electroluminescent material comprising a molecule to cause the electroluminescent material to exhibit a change in light transmittance. In some cases, the molecule is selected from the group consisting of the following molecules, each identified by a first hash block of an InChIKey representation of the molecule:

APZHDSPLWXDLRC,

BCQZLPBUBKOZSS,

BOMJTHPUDZEPFB,

BRLAZTLRRIOAOZ,

CBPFHHWSAJJJMX,

CHEYCWWQWYEBQT,

CRFIXVVATQXIEV,

FIEGOAADWNCJCD,

FOHZCHCZAPFGNM,

GJRJWVFKNPZMFH,

GVZRPOATSVSGAJ,

HLYMCAWWPYGENR,

HNADRWIHKQBHPA,

IAZQZQPAGWVXQI,

IPUBYXNOXMHRIQ,

ITSAWPYMAXGGTC,

JMXAHDFYVDFKGH,

KNJVRORCBOYOFD,

KQYWRHGRGRYRGF,

KXWIDJGUUYJZQO,

LBJNDXHNXHOIOW,

-continued

LNKUDJQQOLKMFV,

NEAKQGPMRGSYKG,

PJZMUZZOUTWQLC,

POHKARBWLJRQMP,

PSYZKNGUTMLXIX,

QAWFUVBQPBMUBP,

QKAAVGQNNXKEOI,

QPCMZRPNBGHOHH,

QQJOWIRVQFJHTG,

QRKBEUXOLZDZIS,

QXOVYVVNXGNNPY,

RJSBRNWTAKKUNE,

UAKJOPZBFONQFS,

UECNXZHCOOYLCZ,

UEHNABXWZLQDEB,

UQFGCCANRNGVSM,

UWKGBUFCOLUTMS,

VATARVYRYVYZOH,

VJVXKLZBPZLKIQ,

WCNNNVCWRYESKA,

WQOSMTXLFOUJTB,

WXIQEEANSYMJCV,

XAAWXWUCWPKXGQ,

XZSXEQWJFCGXEP,

YADNZLJAJJQOFY,

ZOOFJHDVTYSMSM,

ZTTTYNBVNKTWMC,

ZUWBHFRFDLIBCO,

CLGPRTCGCHMHAE,

CZNYNGWGBPMEHI,

CBWWWVHAABHNJY,

UXBZJIBRXGLLNC,

ZWLYCIXGEUTVQL,

LYHASAIOOPIPST,

RZGPWCGZPUHNBV,

JXWVABYSSASQKD,

JPAHDUTVXPSCFW,

FZNGREDDVGPBIU,

JTKNLTCFAXZGRV,

KMNSNJABLNOBKL,

-continued

FKSCQYSGRJKMNI,

UXFQPYLBIFYNAO,

ZGDVSKJMYTYDFX,

CBPYKIAOKVDWPX,

QJAVRZSCHRLIGJ,

ASPDIKWAJQMRCO,

PTFVRTBWIQENON,

QFADIYUJRJQQQU,

JMLOPPZVXIPGMZ,

FGFOKIJGPGXCDY,

HZLLSBCCAOWIHL,

JTKYHXJLZLTZBJ,

CCBZVBVEYZIKPI,

FCHZPVWGTHKKOI,

QOMUCQPTIZNUDB,

QYWGODWKDIOGSX,

RDPVXNNXWKUWQS,

QREZGANIQDOWPI,

QUMHWKYPWYMGBY,

FNDPOTBQLIXHEP,

PAAWKNCADSXJKY,

RHANDXLEIFMQDD,

FOHPQOMVHDSCMT,

UUANYPXXPDKMPJ,

DIHZIJAQHCISIC,

PDUNUPFPWDSZRJ,

VPGQRNDVIATCEN,

GHIQFVANXNJLPR,

BSWVWMPHYWLLNN,

JVRQZQSRHZLZLE,

VMPBRFLTECRQTH,

OEHGGSRMAGICMX,

ULGUGWUFDBIWPQ,

GRPCOGYZIYQJMS,

IMTVACKMXORUMK,

UWDUNMFSWRVPRD,

OZKHDDPBPHPAHD,

YUXQXEOZJBDVCV.

In another aspect, the present disclosure encompasses methods of making one or more of the embodiments described herein, including acetates such as 2-phenyl-2H-pyrazol-3-yl acetate. In still another aspect, the present disclosure encompasses methods of using one or more of the embodiments described herein, including acetates such as 2-phenyl-2H-pyrazol-3-yl acetate.

Other advantages and novel features of the present disclosure will become apparent from the following detailed description of various non-limiting embodiments of the disclosure when considered in conjunction with the accompanying figures.

BRIEF DESCRIPTION OF THE DRAWINGS

Non-limiting embodiments of the present disclosure will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the disclosure shown where illustration is not necessary to allow those of ordinary skill in the art to understand the disclosure. In the figures:

FIGS. 5A-5C illustrate the excitation and orbital separation characteristics based on TD-DFT computation of certain molecular structures, in yet another embodiment;

DETAILED DESCRIPTION

Figure 1:
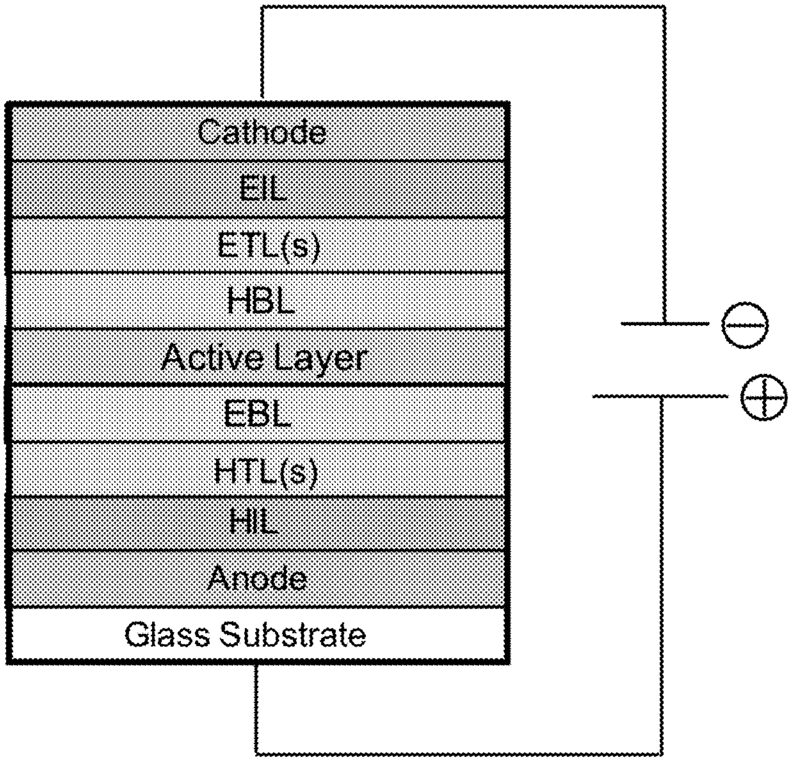
FIG. 1 illustrates an electroluminescent device in accordance with one embodiment of the disclosure.

The present disclosure generally relates to emitting organic molecules, including but not limited to, pyrazoles such as 2-phenyl-2H-pyrazol-3-yl acetate, etc. In some cases, the molecules are able to emit in blue or green wavelengths. In some aspects, such molecules may be used in organic light emitting diodes. In certain embodiments, the molecules may comprise one or more bridge moieties and one or more chromophores. In some embodiments, these molecules can be used as electroluminescent media in devices requiring light emission as a function of applied voltage. Other embodiments of the disclosure are generally directed to systems and devices using such molecules, methods of using such molecules, e.g., to control the emission of light, kits involving such molecules, or the like.

In addition, in certain embodiments, molecules such as those described herein may be electroluminescent, and/or may be useful in electroluminescent media. For instance, the molecules may be compatible with vapor-deposition and/or solution-processed OLED technologies. In one set of embodiments, for example, such molecules may be used in devices which can exhibit a change in light emission due to change in applied voltage. Examples of such devices include indoor or outdoor luminaires, automotive luminaires, displays, or the like.

OLEDs are light-emitting diodes in which the electroluminescent layer is a thin film comprising organic molecules that emit light in response to an electric current. In one embodiment, an OLED may be composed of an organic light-emitting molecule located between two electrodes, an anode and a cathode. The organic molecules may be selected to be conductive due to the delocalization of pi (π) electrons over part or all of the molecule, e.g., such that at least a portion of the molecule exhibits a conjugated system of p orbitals due to the pi electrons. When voltage is applied, positive charges may be introduced via the anode and/or negative charges may be introduced via the cathode. Electrostatic forces may bring the electrons and holes in proximity until they recombine and form an exciton. Radiation can be emitted at a frequency the visible spectrum due to the excited state decay and the subsequent relaxation of the energy levels of the electron. The frequency of this radiation may depend on the mechanism of radiation (e.g., fluorescence, $S_1 \rightarrow S_0$ or phosphorescence, $T_1 \rightarrow S_0$). However, pyrazoles such as 2-phenyl-2H-pyrazol-3-yl acetate have not been previously been identified as being suitable for OLEDs or similar applications.

Thus, one aspect as discussed herein is generally directed to systems and methods of electrically controlling the emission of light. In some embodiments, these may include molecules that can produce light in the blue or green region of the visible spectrum when they are excited via electric current. For example, in some cases, the molecules may comprise one or more conjugated groups and a pyrazole (or similar) bridge moiety. Such optoelectronic molecules can be used in electroluminescent media, where the amount of light emission is controllable by applying voltages. For example, the optoelectronic molecule may exhibit light emission at varying biases. In some cases, a variety of different voltages can be applied to control the light emission of the electroluminescent media.

Pyrazoles are nitrogen-containing five membered pi (π)-conjugated molecules that have been used as building blocks in a wide range of biologically active molecules. Pyrazoles are easily functionalized leading to the facile construction of library of compounds that display tunable properties. These compounds have been extensively studied and used in the context of medicinal chemistry, but have not been used as electroluminescent materials or in OLED devices.

Thus, as discussed herein, such optoelectronic molecules can be used in electroluminescent media, where the amount of light absorbance or transmittance is controllable by applying voltages. For example, the optoelectronic molecule may exhibit a first light transmittance at a first voltage (e.g., including 0 V), and a second light transmittance at a second voltage different from the first. In some cases, a variety of different voltages can be applied to control the light absorbance or transmittance of the electroluminescent media.

For instance, certain embodiments are generally directed to emitting organic molecules. In some embodiments, the molecules may comprise one or more bridge moieties and one or more chromophores in certain cases.

The molecules may comprise two or more chromophores bridged by a pyrazole (or similar) bridge moiety. The bridge may be a pi (π)-conjugated moiety that can be covalently linked between two or more chromophore moieties. The donor may be a moiety that is able to donate an electron from its highest occupied molecular orbital (HOMO). The acceptor may be a moiety that is able to accept an electron in its lowest unoccupied molecular orbital (LUMO). Without wishing to be bound by any theory, it is believed that the bridge moiety can, in some embodiments, enhance fluorescence from the molecule, impart steric rigidity to the molecule, and/or restrict the donor and acceptor moieties into specific configurations. This may lead to delocalization of electronic states in the linked donor and acceptor and/or may prevent overlap between the conjugated pi systems of the donor and acceptor moieties.

Accordingly, some aspects of the present disclosure are generally directed to pyrazoles such as 2-phenyl-2H-pyrazol-3-yl acetate, etc. Pyrazoles have not generally been identified as being suitable optoelectronic molecules, e.g., for use within electroluminescent media. However, it has been found that certain types of pyrazoles are able to absorb visible (400-700 nm) light and/or near-infrared light (e.g., wavelengths of 700-2500 nm) in response to applied voltages, and/or emit in blue or green wavelengths (e.g., wavelengths of 450-600 nm).

In addition, in some embodiments, certain types of pyrazoles are able to emit light at wavelengths of between 350 nm and 900 nm, or in the near-UV range (e.g., between 300 nm and 400 nm). In some cases, the pyrazoles are able to emit light at wavelengths of at least 300 nm, at least 350 nm, at least 400 nm, at least 450 nm, at least 500 nm, at least 550 nm, at least 600 nm, at least 650 nm, at least 700 nm, at least 750 nm, at least 800 nm, and/or no more than 900 nm, no more than 850 nm, no more than 800 nm, no more than 750 nm, no more than 700 nm, no more than 650 nm, no more than 600 nm, no more than 550 nm, no more than 500 nm, no more than 450 nm, no more than 400 nm, etc. Combinations of any of these ranges are also possible.

In one set of embodiments, for instance, a pyrazole may have a structure:

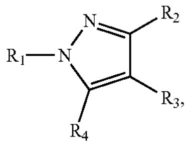

wherein each of $R_1$, $R_2$, $R_3$ and $R_4$ independently comprises a phenyl moiety, or is —H, —OCHO, —$NO_2$, —CN, —$OCH_3$, —$CH_2OCH_3$, —$CH_3$, —OR', —$CH_2OR'$, —R', or —OC(O)R, where R' can be an alkyl or phenyl moiety. For example, in certain embodiments, two of $R_1$, $R_2$, $R_3$ and $R_4$ each independently comprises a conjugated system. In some embodiments, three of $R_1$, $R_2$, $R_3$ and $R_4$ each independently comprises a conjugated system, and in some embodiments, each of $R_1$, $R_2$, $R_3$ and $R_4$ each independently comprises a conjugated system. For example, in certain embodiments, four of $R_1$, $R_2$, $R_3$ and $R_4$ each independently comprises a conjugated system. In some embodiments, at least two of the groups represented by $R_1$, $R_2$, $R_3$, and $R_4$ may comprise a conjugated system.

Thus, as a non-limiting example, in one embodiment, the pyrazole may have a structure:

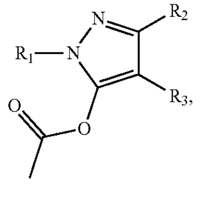

i.e., when $R_4$ is —$OCOCH_3$.

In some cases, one or more of the phenyl moieties represented by $R_1$, $R_2$, $R_3$, or $R_4$ may independently be selected from groups such as a phenyl group, a naphthyl group, an anthracene group, a fluorenyl group, or the like, a heterocyclic group (such as a furyl group, a pyrrolyl group, a thiazolyl group, an oxazolyl group, an imidazolyl group, a pyridyl group, a pyrazinyl group, a pyrimidinyl group, a pyrazolyl group, etc.), or the like. In certain embodiment, a phenyl moiety may have a structure:

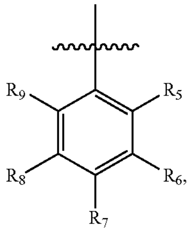

where $R_5$, $R_6$, $R_7R_8$, and $R_9$ may each independently be selected from one or more of the following. For example, an R moiety (e.g., $R_5$, $R_6$, $R_7R_8$, and $R_9$) may be —H or be selected from an alkyl (such as a methyl group, an ethyl group, a propyl group, a butyl group, or the like), a cycloalkyl (such as a cyclopropyl group, a cyclobutyl group or a cyclopentyl group, a cyclohexyl group, etc.), an aromatic (such as phenyl group, a naphthyl group, an anthracene group, a fluorenyl group, or the like), a heterocyclic (such as an epoxide group, a furyl group, a pyrrolyl group, a thiazolyl group, an oxazolyl group, an imidazolyl group, a pyridyl group, a pyrazinyl group, a pyrimidinyl group, a piperidinyl group, a pyrazolyl group, etc.), a hydroxyl, an alkoxy (such as a methoxy, an ethoxy or similar), an amine such as —$NH_2$, an alkylamine (such as methyl amine, ethyl amine propyl amine or the like), a dialkylamine (such as dimethyl amine, diethylamine, or diisopropyl amine, etc.) an arylamine (such as phenyl amine, naphthyl amine, etc.), a diarylamine (such as diphenyl amine or the like), a nitro group or a halogen such as Br, Cl or F.

In certain embodiment, an aryl moiety may have the following structures such as:

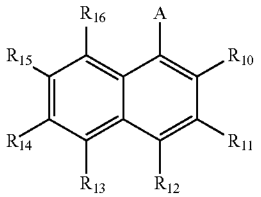

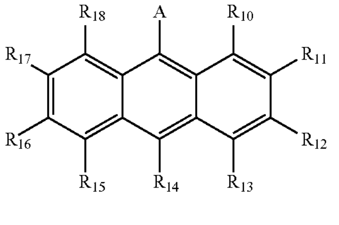

-continued

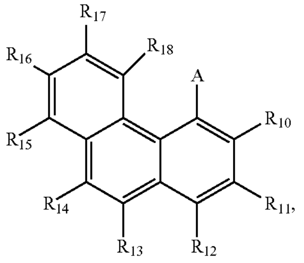

where $R_{10}$, $R_{11}$, $R_{12}$, $R_{13}$, $R_{14}$, $R_{15}$, $R_{16}$, $R_{17}$, or $R_{18}$ may each independently be selected from one or more of the following. For example, an R moiety (e.g., any one or more of $R_{10}$, $R_{11}$, $R_{12}$, $R_{13}$, $R_{14}$, $R_{15}$, $R_{16}$, $R_{17}$, or $R_{18}$) may independently be —H or be selected from an alkyl (such as a methyl group, an ethyl group, a propyl group, a butyl group, or the like), an aromatic (such as phenyl group, a naphthyl group, an anthracene group, a fluorenyl group, or the like), a heterocyclic (such as an epoxide group, a furyl group, a pyrrolyl group, a thiazolyl group, an oxazolyl group, an imidazolyl group, a pyridyl group, a pyrazinyl group, a pyrimidinyl group, a piperidinyl group, a pyrazolyl group, etc.), a hydroxyl, an alkoxy (such as a methoxy, an ethoxy or similar), an amine such as —$NH_2$, an alkylamine (such as methyl amine, ethyl amine propyl amine or the like), a dialkylamine (such as dimethyl amine, diethylamine, or diisopropyl amine, etc.) an arylamine (such as phenyl amine, naphthyl amine, etc.), a diarylamine (such as diphenyl amine or the like), a nitro group or a halogen such as Br, Cl or F.

In certain embodiment, an aryl moiety may have the following structures such as:

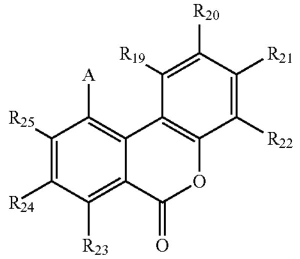

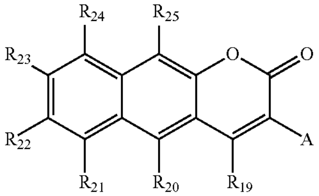

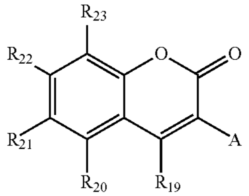

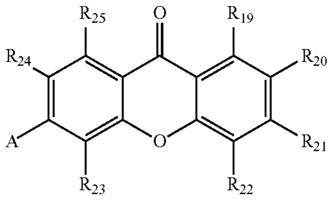

-continued

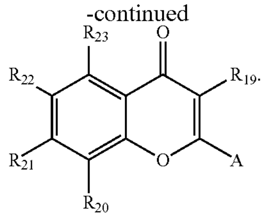

where $R_{19}$, $R_{20}$, $R_{21}$, $R_{22}$, $R_{23}$, $R_{24}$, or $R_{25}$ may each independently be selected from one or more of the following. For example, an R moiety (e.g., any one or more of $R_{19}$, $R_{20}$, $R_{21}$, $R_{22}$, $R_{23}$, $R_{24}$, or $R_{25}$) may independently be —H or be selected from an alkyl (such as a methyl group, an ethyl group, a propyl group, a butyl group, or the like), a hydroxyl, an alkoxy (such as a methoxy, an ethoxy or similar), an amine such as $—NH_2$, an alkylamine (such as methyl amine, ethyl amine propyl amine or the like), a dialkylamine (such as dimethyl amine, diethylamine, or diisopropyl amine, etc.) an arylamine (such as phenyl amine, naphthyl amine, etc.), a diarylamine (such as diphenyl amine or the like), a nitro group or a halogen such as Br, Cl or F.

One representative non-limiting example of such a pyrazole compound is shown below, where $R_1$, $R_2$, and $R_3$ are each independently substituted phenyl derivatives:

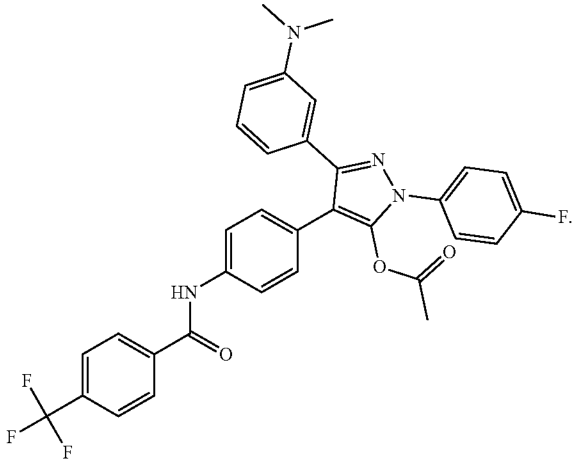 [SMILES: CC(=O)Oc1c(-c2ccc(NC(=O)c3ccc(C(F)(F)F)cc3)cc2)c(-c2cccc(N(C)C)c2)nn1-c1ccc(F)cc1]

Still other non-limiting examples of potentially suitable molecules, including pyrazoles such as 2-phenyl-2H-pyrazol-3-yl acetate, are shown in FIGS. 7-19. Each structure is identified by the first hash block (14 characters) of the InChIKey (International Chemical Identifier Key) of the molecule's structure (i.e., its connectivity information). Those of ordinary skill in the art will be familiar with the InChI system and its related InChIKey hashes.

In some aspects, molecules such as any of those described herein may be contained within an electroluminescent device. Examples of such devices include, but are not limited to, indoor or outdoor luminaires, display devices, as well as molecular systems for digital information processors, optical recording, thermal writing displays, laser printers, infrared photography, or the like. An example of an electroluminescent device is shown in FIG. 1. However, it should be understood that this is by way of example only. In other embodiments, the electroluminescent device may have different structures or electrical configurations, etc. The electroluminescent device also need not be transparent or designed to allow light to pass through; an example of such a device is a transparent display.

In one set of embodiments, an electroluminescent device may comprise a cathode and anode, over which a voltage can be applied. Any suitable voltage can be applied, e.g., at least 1 V, at least 3 V, at least 5 V, at least 10 V, at least 30 V, at least 50 V, at least 100 V, etc. The voltage may be used to cause the flow of electrons from the cathode to the active layer and positive charges (holes) to flow from the anode to the active layer. As a non-limiting example, FIG. 1 shows an electroluminescent device comprising of both an anode and cathode with various organic layers between.

One or both of these electrodes may be substantially transparent in certain cases, e.g., to allow a substantial amount of light to pass through the electrode, at least in the visible range. For instance, an electrode may allow at least 50%, at least 70%, or at least 90% of the incident visible light to pass through. For instance, an electrode may be made from a substantially transparent material, such as indium tin oxide (ITO), ZnO:F, ZnO:Al, ZnO:Ga, ZnO:B, ZnO:In, $In_2O_3$:Sn, $Cd_2SnO_4$, $SnO_2$:Sb, conjugated polymers (such as PEDOT:PSS), silver nanowires, graphene, or other materials. However, in some embodiments, one or both of the electrodes may be made out of materials that are not substantially transparent, for example, metals such as platinum, gold, silver, or copper, or conductive non-metals such as carbon. In some cases, materials that are not substantially transparent may nonetheless be used, e.g., in embodiments where the electrode is substantially transparent, or where light is allowed to pass through the device; for example, the electrode may be formed as a mesh or other structure containing openings that allows at least some light to pass through. In addition, it should be understood that an electrode need not be substantially transparent in all embodiments, and that the electrodes within a device may have the same or different amounts of light transparency.

In some cases, the electroluminescent material is present in a separate region that is in direct contact with both electrodes. However, other configurations are possible. For example, there may be one or more other regions (e.g., layers) intervening between the layer containing the electroluminescent material and the cathode and/or anode. As an example, in FIG. 1, multiple layers of organic or inorganic materials may be deposited as thin layers between the active layer and an electrode. These include the EIL (electron injection layer), the ETL (electron transport layer), the HBL (hole blocking layer), the EBL (electron blocking layer), the HTL (hole transport layer), and the HIL (hole injection layer. However, it should be understood that none of these layers are required to be present, and in other embodiments, a variety of other arrangements of layers between the cathode and the anode are also possible. In other cases, the electroluminescent material may be in direct contact with the working electrode.

In some cases, the electroluminescent region may be relatively thin, for example, as a layer or a coating adjacent to an electrode. For instance, in some cases, the region may have a cross-sectional thickness of less than 1 mm, less than 500 micrometers, less than 300 micrometers, less than 100 micrometers, less than 50 micrometers, less than 30 micrometer, less than 10 micrometers, less than 5 micrometers, less than 3 micrometers, less than 1 micrometer, less than 500 nm, less than 300 nm, less than 100 nm, less than 50 nm, less than 30 nm, less than 10 nm, or less than 5 nm. Without wishing to be bound by any theory, it is believed that thinner regions may allow for more penetration of charges created at the electrodes. However, the electroluminescent region may also have sufficient thickness so as to exhibit light emission, e.g., when a voltage is applied.

For instance, in FIG. 1, the layer EBL is shown to be adjacent to electroluminescent region (active layer) containing the electroluminescent material, and when a voltage is applied, positive ions are able to flow from the anode to the electroluminescent region while simultaneously blocking the flow of electrons from reaching the anode. Similarly, the layer EBL is shown to be adjacent to an electroluminescent region (active layer) containing the electroluminescent material, and when a voltage is applied, negative ions are able to flow from the cathode to the electroluminescent region while simultaneously blocking the flow of holes from reaching the cathode. However, as noted above, in other cases, the electroluminescent region may not comprise additional layers, and the electroluminescent materials may be located adjacent to the electrodes within the device.

Examples of hole transporting, injecting, or blocking materials include, but are not limited to, tris(4-carbazoyl-9-ylphenyl)amine (TCTA), 1,1-bis [(di-4-tolylamino)phenyl] cyclohexane (TAPC), $MoO_3$ 1,4,5,8,9,11-hexaazatriphenylenehexacarbonitrile (HATCN), and the like. Examples of electron transporting/injecting/blocking materials include, but are not limited to, LiF, 1,3,5-Tris(3-pyridyl-3-phenyl)benzene (TmPyPB), tris(8-hydroxyquinoline)aluminum(III) (Alq3), bathophenanthroline (BPhen), and the like.

In addition, in certain embodiments, the electroluminescent device may also be contained within a suitable protective media. For example, the use of an encapsulant can have a beneficial impact on the lifespan of the device, reducing molecular oxygen and water from reaching electrochemically active sites during device operation. The protective media may be, for example, glass, plastics, UV-curable epoxies, or the like, and in certain embodiments, the protective media may be non-conductive. Examples of other protective media include, but are not limited to, polycarbonate, acrylic, polyvinyl chloride (PVC), polyethylene terephthalate glycol-modified (PETG), cyclic olefin copolymer, liquid silicon rubber, polyethylene, ionomer resin, transparent polypropylene, fluorinated ethylene propylene, styrene methyl methacrylate, styrene acrylonitrile resin, etc.

U.S. Provisional Application Ser. No. 63/359,290, filed on Jul. 8, 2022, entitled "Pyrazole Compounds for Organic Light Emitting Diodes and Other Applications," is incorporated herein by reference in its entirety.

The following examples are intended to illustrate certain embodiments of the present disclosure, but do not exemplify the full scope of the disclosure.

Example 1

Figure 2:
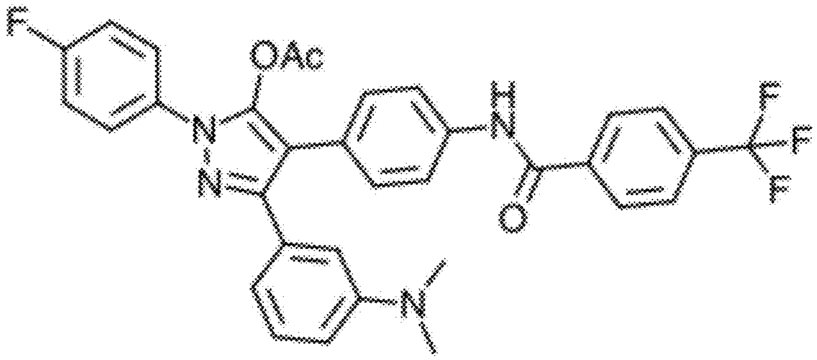
FIG. 2 illustrates a structure in accordance with one embodiment.
Figure 3:
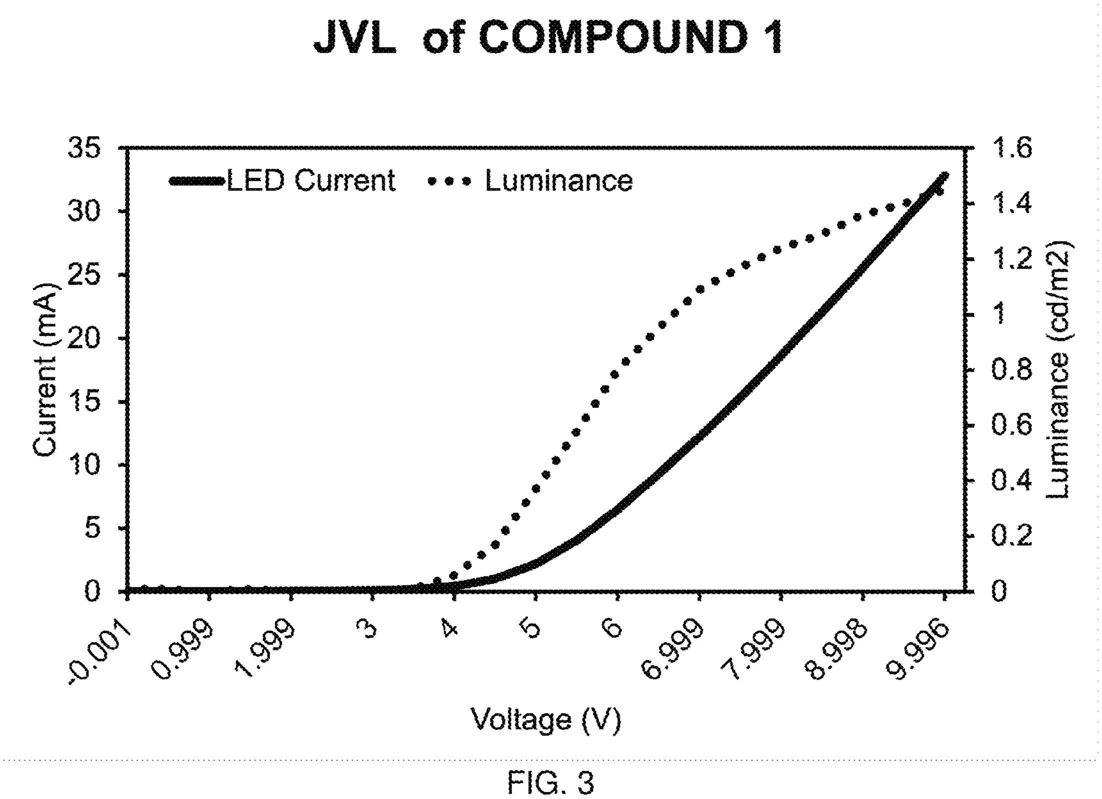
FIG. 3 illustrates various properties of the structure shown in FIG. 2, in yet another embodiment.

One embodiment contemplates a molecule having formula $C_{33}H_{26}F_4N_4O_3$ and exhibiting electroluminescence with emission in the blue part of the visible spectrum in the range of 420 nm to 600 nm (FIG. 2). This structure is shown in FIG. 2 and identified as Compound 1. FIG. 3 shows the JVL (current density/voltage/luminance) curve for this molecule in a solution-processed device.

FIG. 5A illustrates the molecular structure of a pyrazole-based blue emitter. FIG. 5B shows schematic diagram of energy levels with corresponding wavelengths and contributions of molecular orbitals computed using a quantum chemistry software. FIG. 5C shows the computed frontier electronic orbitals for the molecule shown in FIG. 5A.

Example 2

Figure 4:
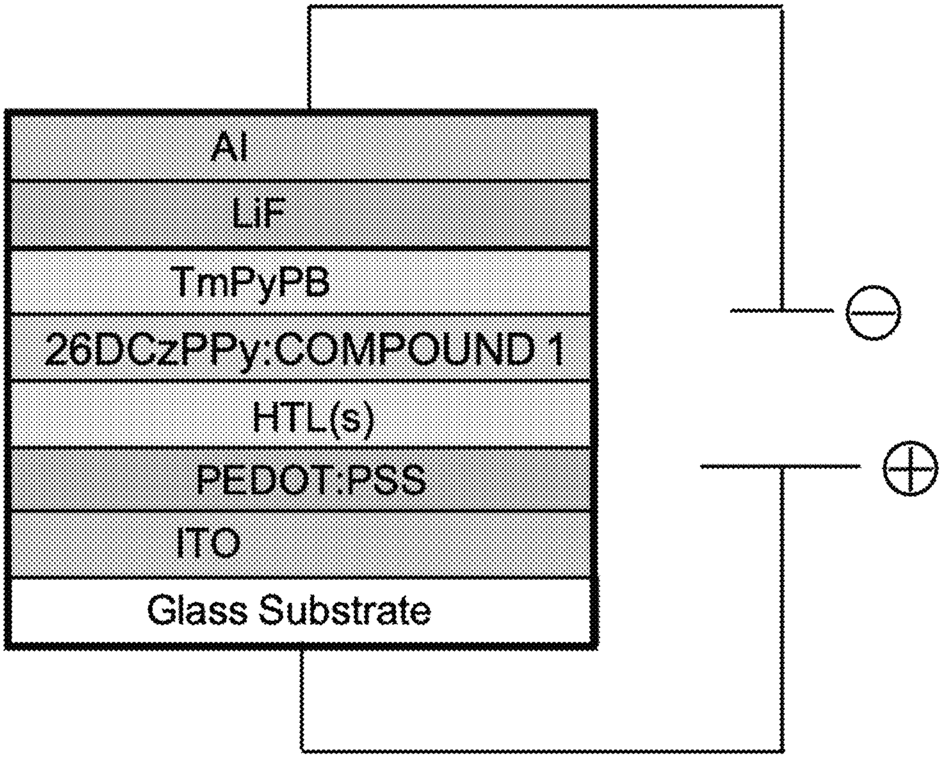
FIG. 4 illustrates an electroluminescent device using the structure shown in FIG. 2, in accordance with another embodiment.

One non-limiting example of a device is shown in FIG. 4, showing a schematic architecture of an embodiment of the device using the molecule shown in FIG. 2 ("Compound 1"). This device comprises:

1. A glass substrate
2. A transparent electrode, for example, indium tin oxide (ITO)
3. A hole injection material, for example, a semiconducting polymer such as PEDOT:PSS, or an organic molecule, for example, 1,4,5,8,9,11-hexaazatriphenylene-hexacarbonitrile (HATCN)
4. An electroluminescent OLED dispersed in a host matrix, for example, 2,6-bis(3-(carbazol-9-yl)phenyl) pyridine (26DCzPPy):Compound 1 (5 wt %)
5. An electron transport material, for example, 1,3,5-tris (3-pyridyl-3-phenyl)benzene (TmPyPB)
6. An electron injection material, for example, lithium fluoride
7. A top electrode, for example, aluminum.

Example 3

Synthesis of a representative example is as shown in the following:

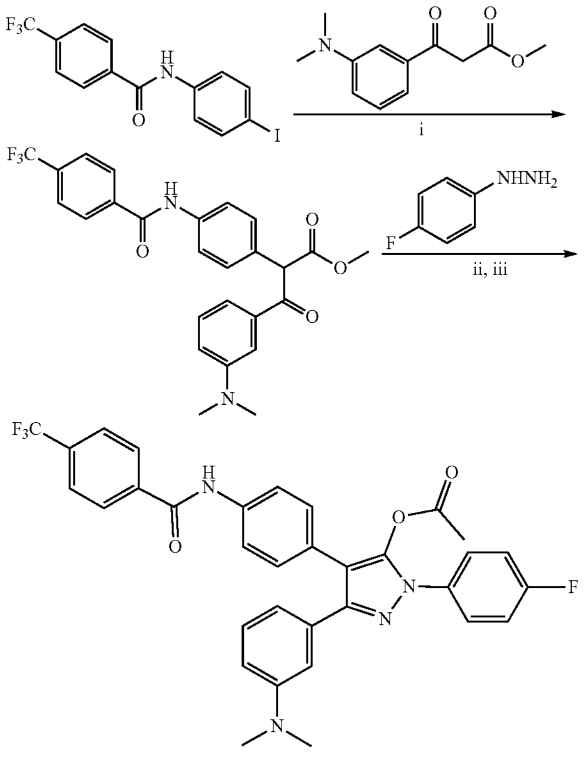

Reaction conditions: (i) CuI, L-proline, $Cs_2CO_3$, DMSO, 40-50° C.; (ii) T3P (propanephosphonic acid anhydride), MW, ethylacetate, 100° C., 5 min; (iii) AcCl, pyridine, dioxane, room temperature A three-step process starting with the reaction of substituted β (beta)-ketoester with a suitably substituted aryl halide in presence of Cu (see Xie, et al., "CuI/l-Proline-Catalyzed Coupling Reactions of Aryl Halides with Activated Methylene Compounds," *Org. Lett.,* 7(21):4693-4695, 2005) defines the substituent at position 4 of the pyrazole ring. Condensation with hydrazine derivative using propylphosphonic anhydride (T3P) under microwave conditions construct the 3-hydroxy pyrazole core (see Desroses, et al., "A Convenient Microwave-Assisted Propylphosphonic Anhydride (T3P®) Mediated One-Pot Pyrazolone Synthesis," *Eur. J. Org. Chem.,* 26:5879-5885, 2013). The final acetylation of the 3-hydroxy can be achieved by acetyl chloride in the presence of pyridine in dioxane at room temperature (see Szilagyi, et al., "Studies on Pyridazine Compounds, XIV. Cyclization of Pyridazinylhydrazones," *Heterocycles,* 20(5):765-770, 1983).

Availability of a range substituted aryl halides, and hydrazine derivatives makes this synthetic route viable to access differently substituted pyrazoles. A two-step synthetic approach from substituted acetophenones and dimethyl carbonate in presence of sodium hydride in toluene under reflux conditions is described in Borowiecki, et al., "Synthesis of novel proxyphylline derivatives with dual Anti-*Candida albicans* and anticancer activity," *Eur. J. Med. Chem.,* 150: 307-333, 2018. This can be used for a variety of aryl substituted beta-keto esters.

Another approach is a general synthetic pathway towards 1,2,3,5-tetrasubstituted pyrazoles via a one-pot four component, coupling-addition-cyclocondensation-halogenation and Suzuki reaction sequence as reported by Willy, B., et al., "Rapid One-Pot, Four-Step Synthesis of Highly Fluorescent 1,3,4,5-Tetrasubstituted Pyrazoles," *Org. Lett.,* 13(8):2082-2085, 2011.

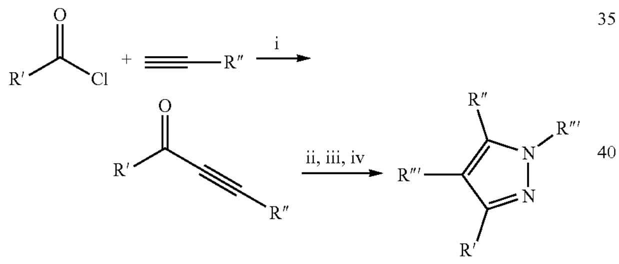

Reaction conditions: (i) $PdCl_2(PPh_3)_2$, CuI, $NEt_3$, THF, 1 h, rt; (ii) R''''$NHNH_2$, tBuOH, 10 min. 150° C.; (iii) NBS (30 min., rt); (iv) R''''$B(OH)_3$, $K_2CO_3$, $PPh_3$, $H_2O$, 20 min., 160° C., (MW). A suitable combination of the starting materials allow the synthesis of a huge variety of pyrazoles with tetrasubstitution.

Example 4

In this example, computational modeling was applied to select for the most promising candidates. In particular, time-dependent density functional theory (TD-DFT) was used, which provides estimates of molecular excited state energies and absorbance. The TD-DFT calculations were run with the B3LYP functional with the Def2-TZVP basis set using the Turbomole software package.

Figure 6:
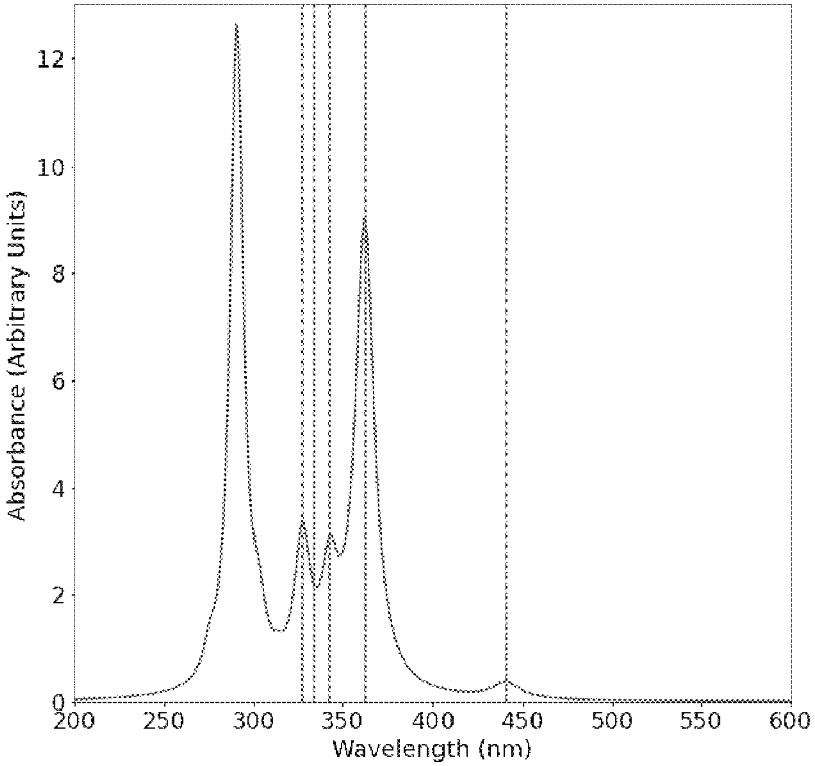
FIG. 6 illustrates a UV-Vis spectrum of the structure shown in FIG. 2, based on TD-DFT, in another embodiment.
Figure 7:
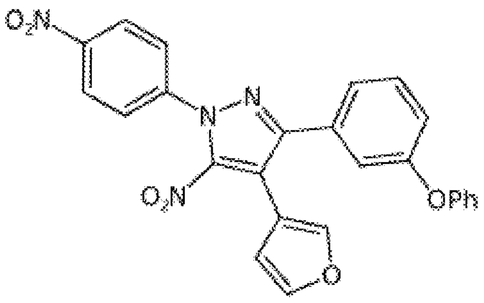
FIGS. 7-19 illustrate certain additional molecules, in accordance with other embodiments.
Figure 7:
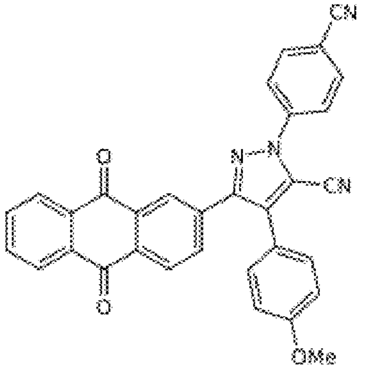
Figure 7:
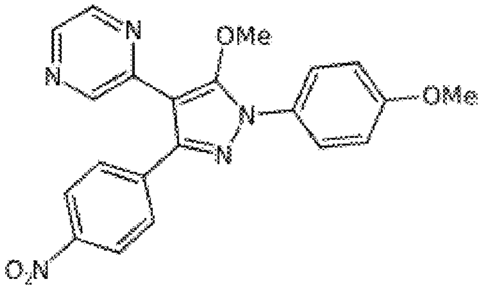
Figure 7:
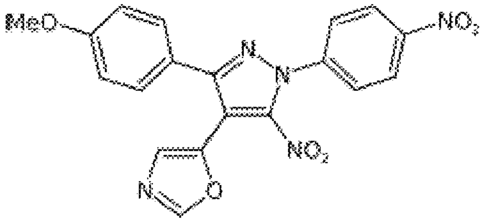
Figure 7:
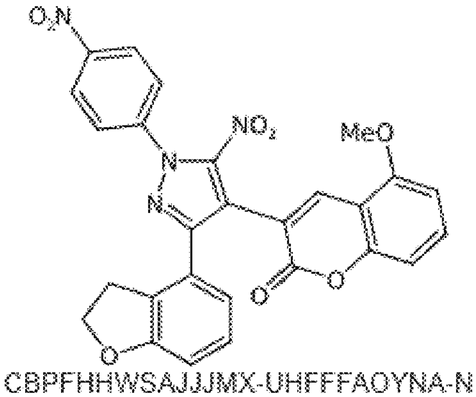
Figure 7:
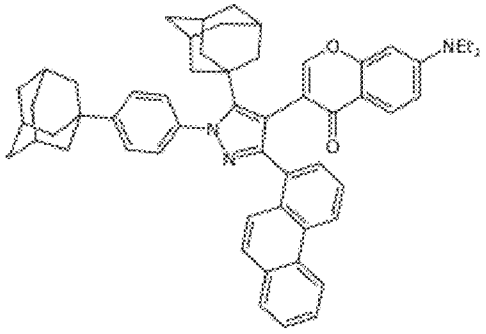
Figure 7:
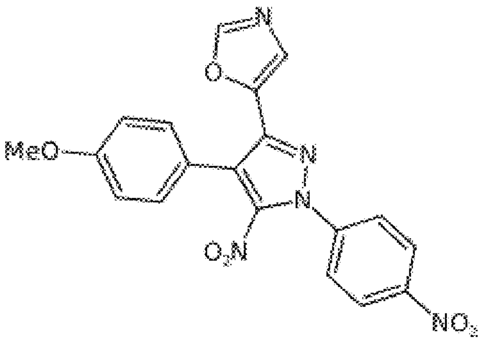
Figure 7:
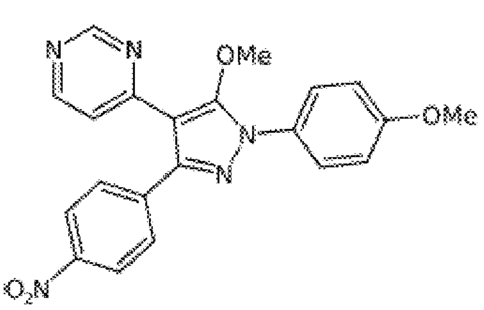
Figure 8:
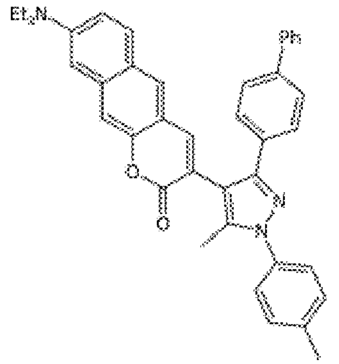
Figure 8:
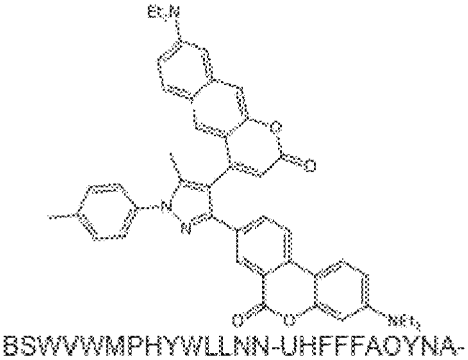
Figure 8:
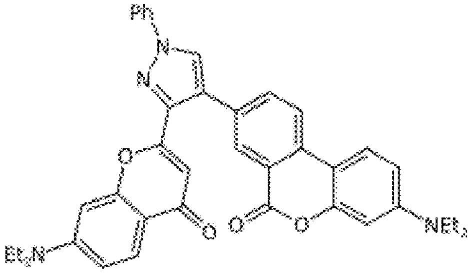
Figure 8:
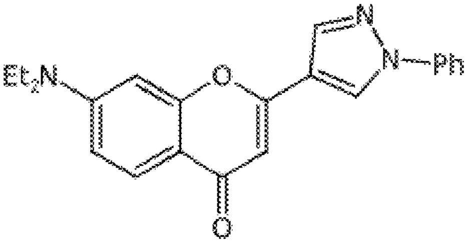
Figure 8:
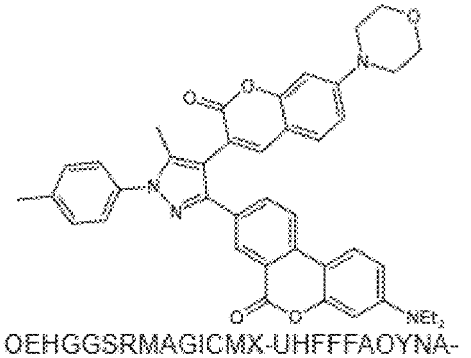
Figure 8:
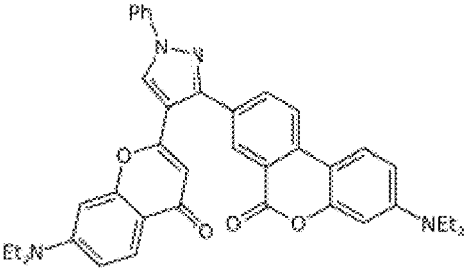
Figure 8:
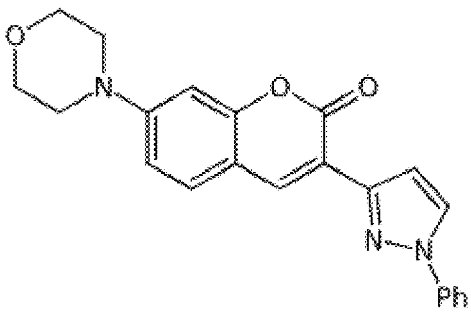
Figure 8:
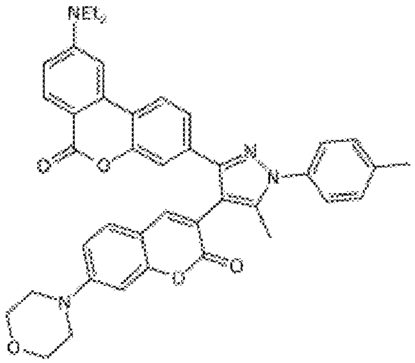
Figure 9:
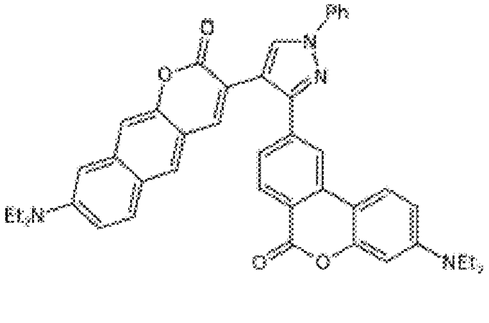
Figure 9:
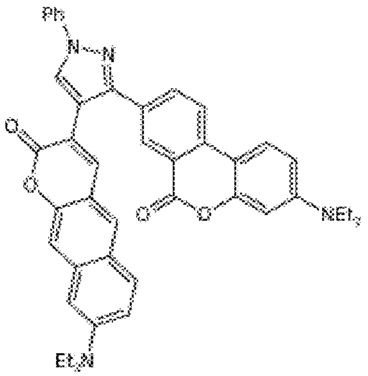
Figure 9:
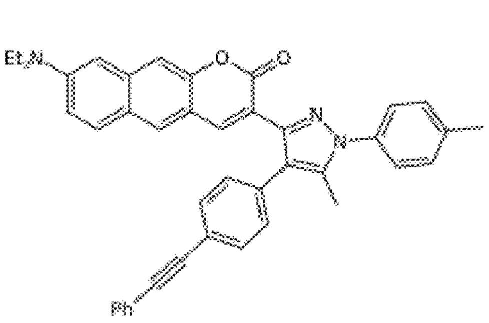
Figure 9:
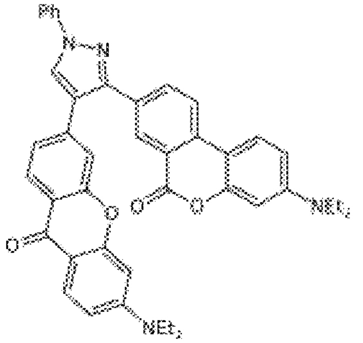
Figure 9:
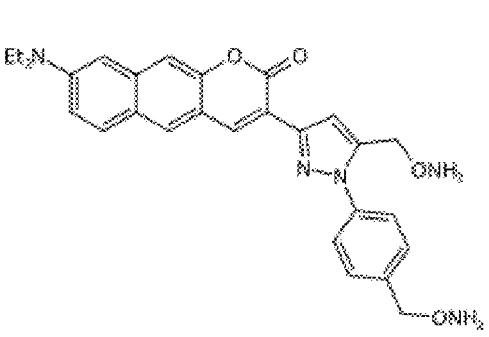
Figure 9:
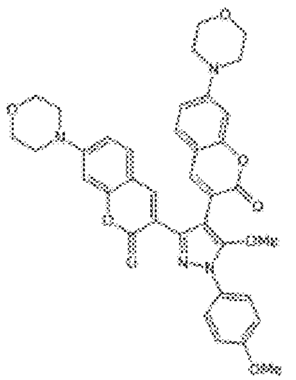
Figure 9:
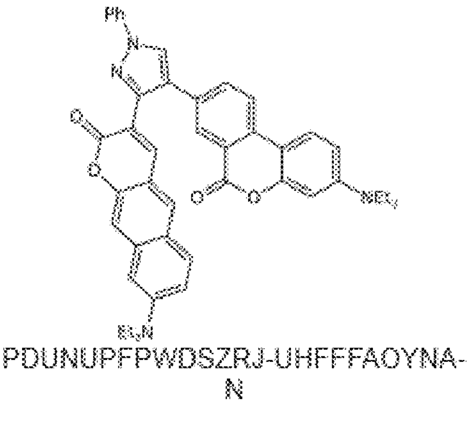
Figure 9:
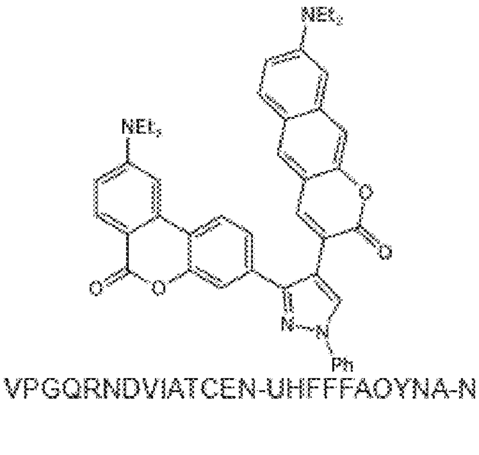
Figure 10:
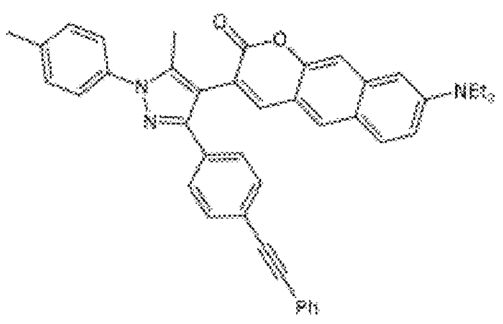
Figure 10:
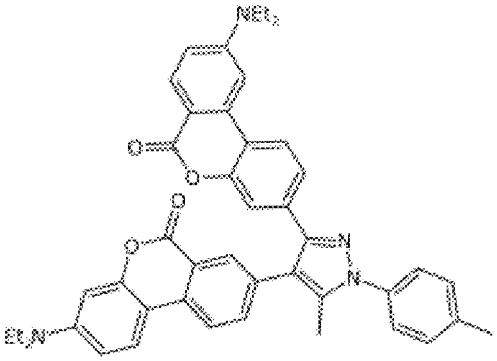
Figure 10:
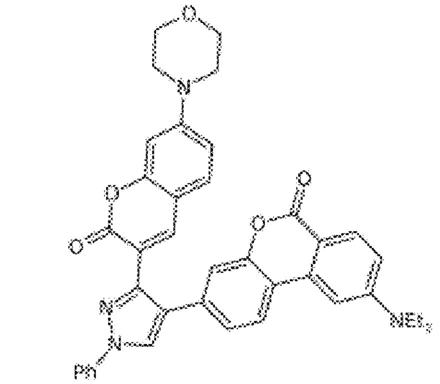
Figure 10:
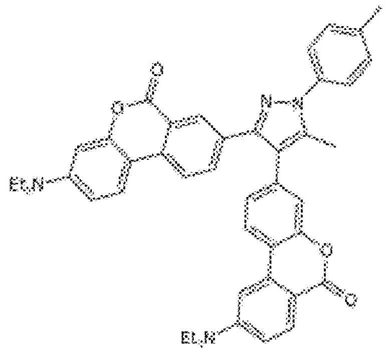
Figure 10:
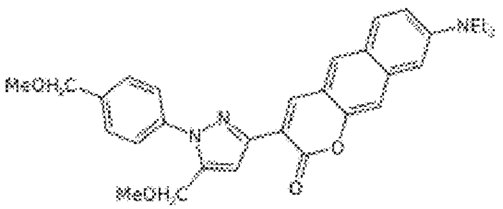
Figure 10:
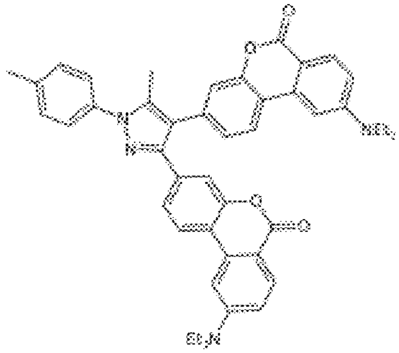
Figure 10:
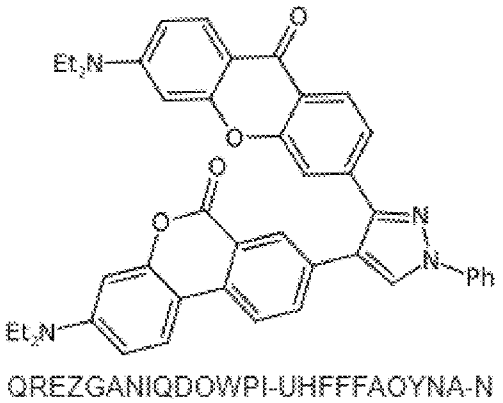
Figure 10:
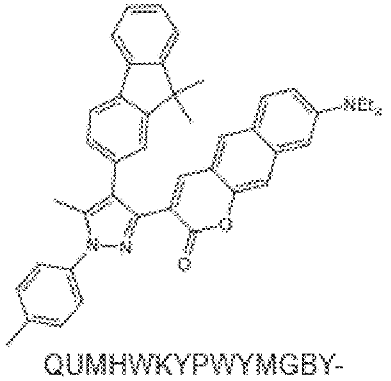
Figure 11:
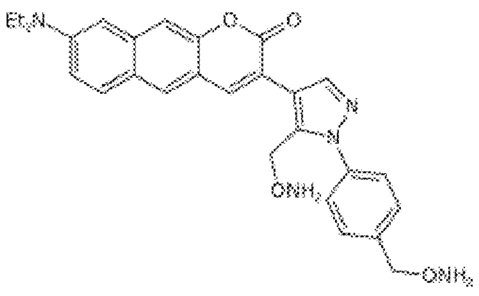
Figure 11:
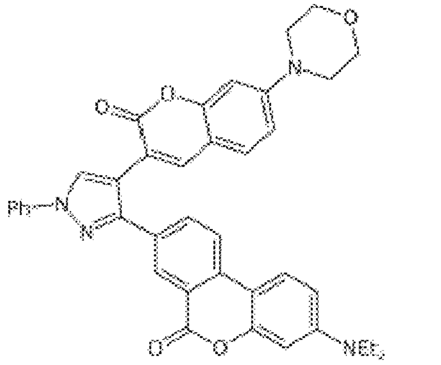
Figure 11:
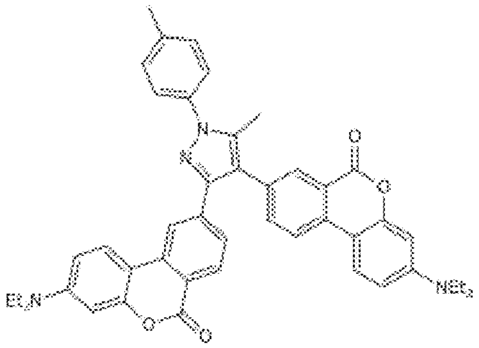
Figure 11:
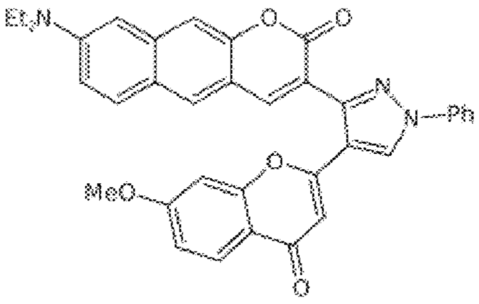
Figure 11:
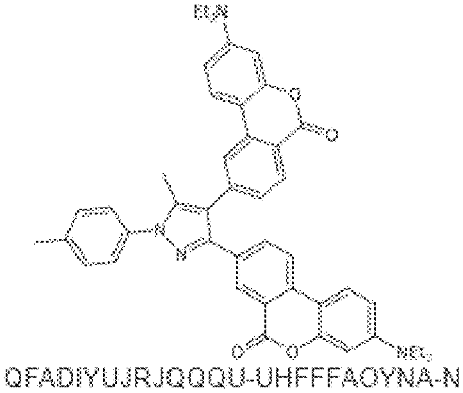
Figure 11:
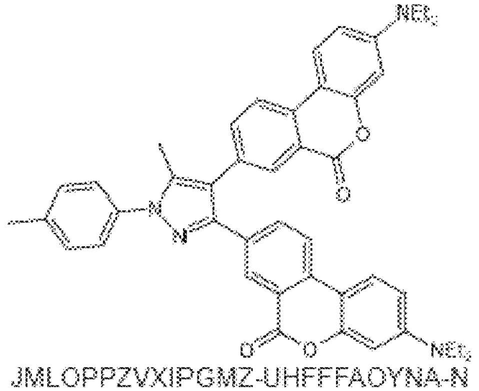
Figure 11:
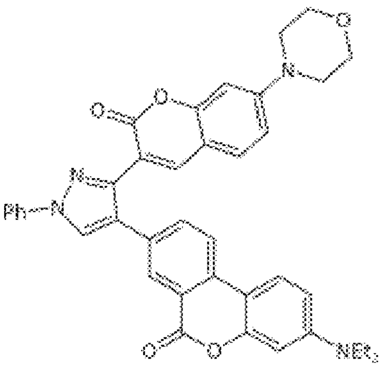
Figure 11:
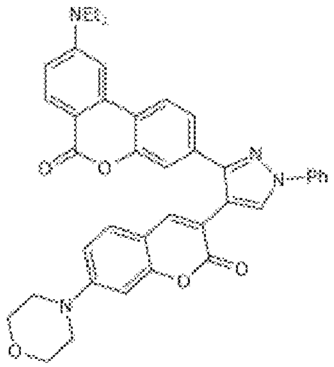
Figure 12:
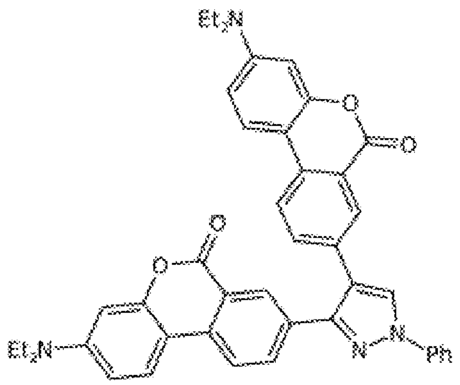
Figure 12:
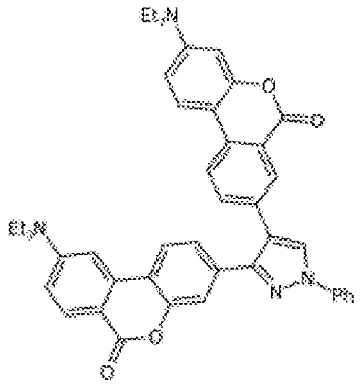
Figure 12:
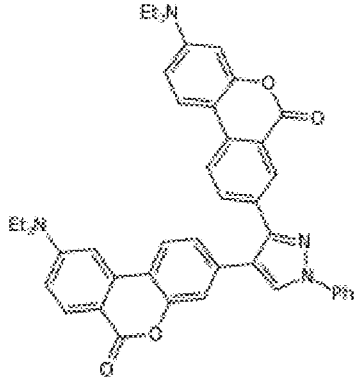
Figure 12:
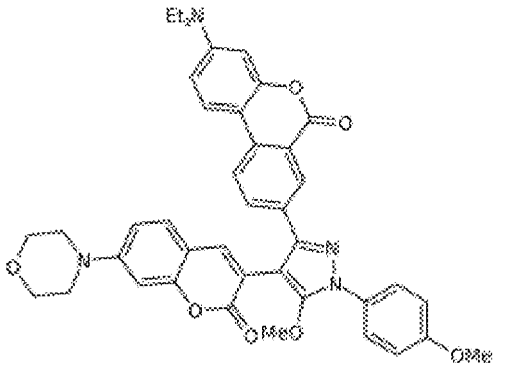
Figure 12:
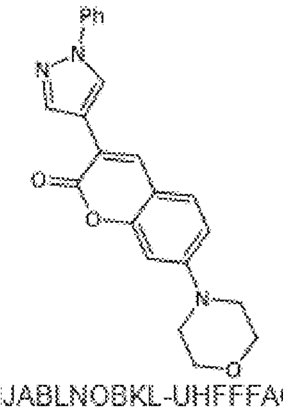
Figure 12:
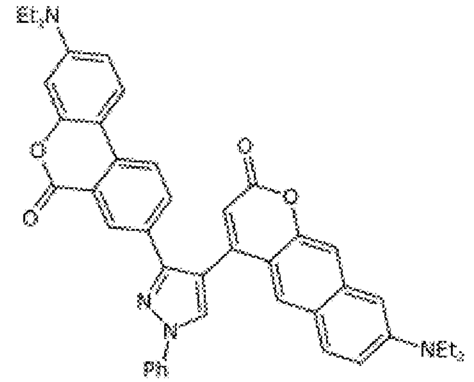
Figure 12:
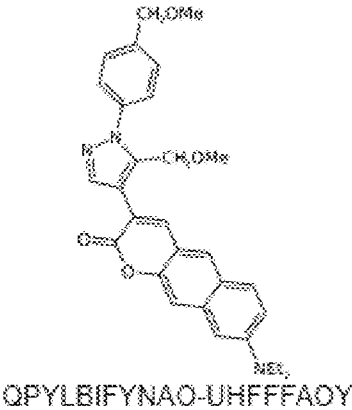
Figure 12:
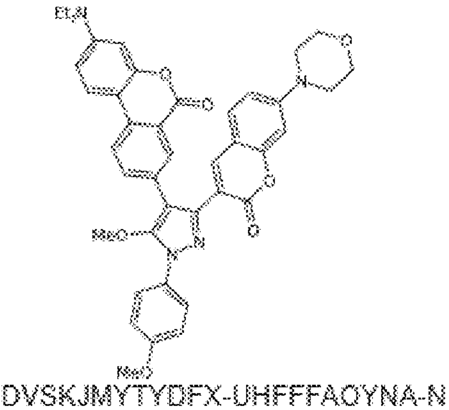
Figure 13:
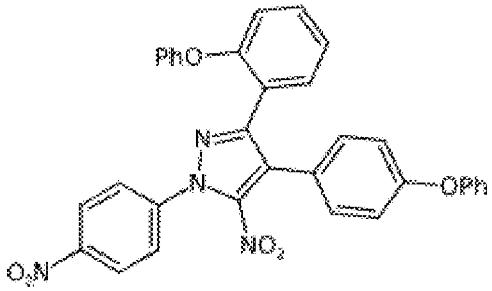
Figure 13:
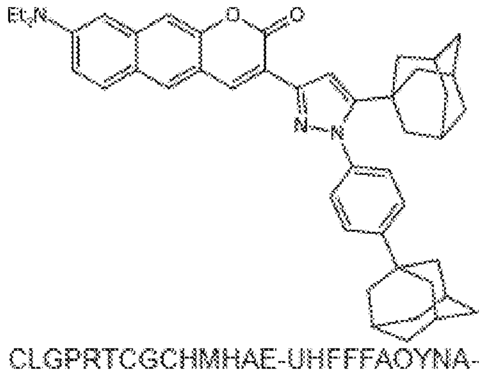
Figure 13:
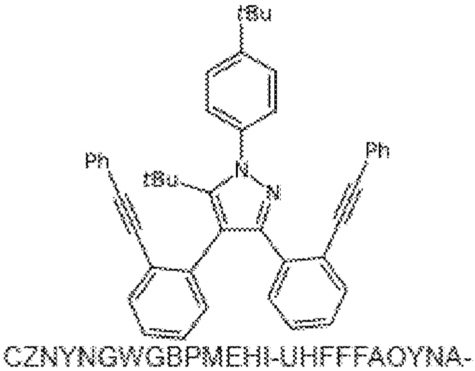
Figure 13:
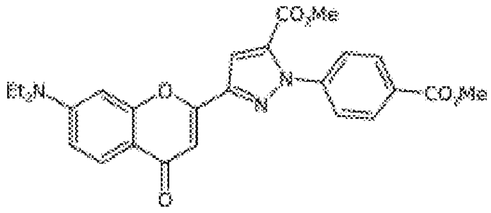
Figure 13:
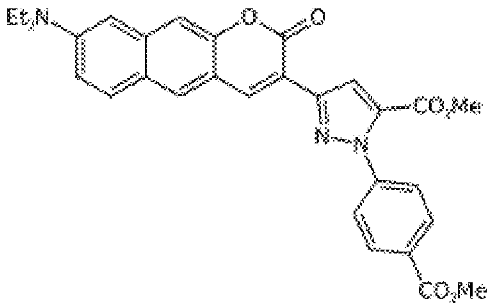
Figure 13:
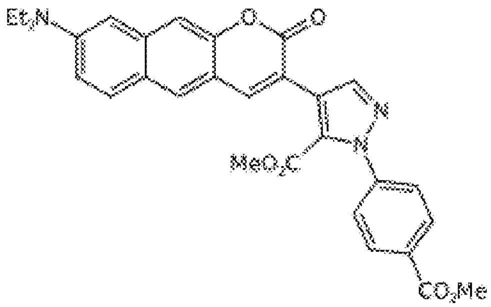
Figure 13:
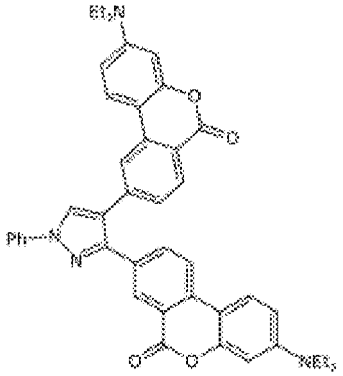
Figure 13:
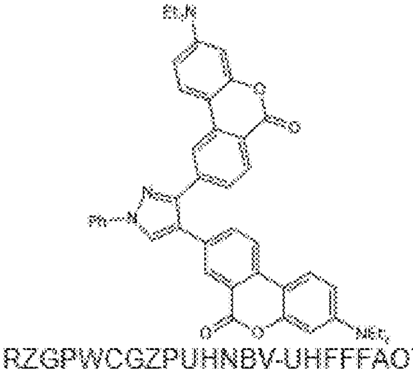
Figure 14:
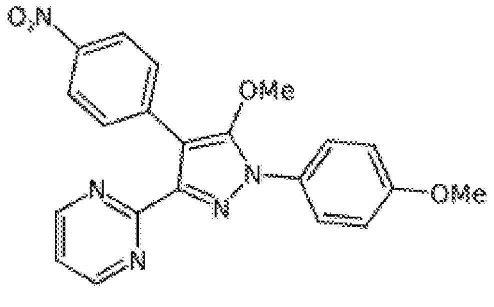
Figure 14:
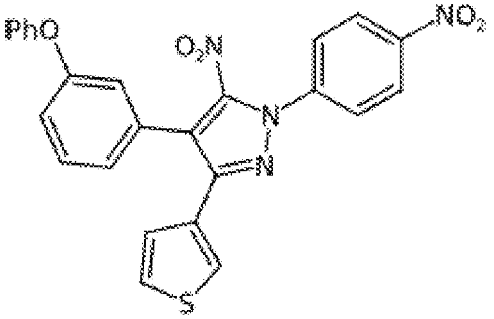
Figure 14:
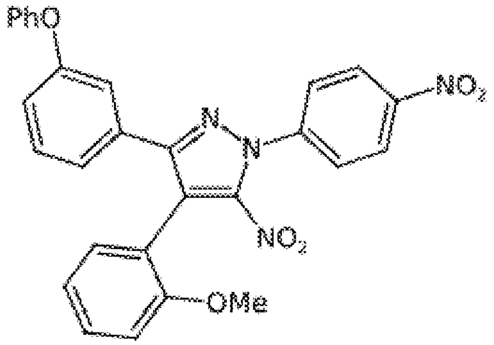
Figure 14:
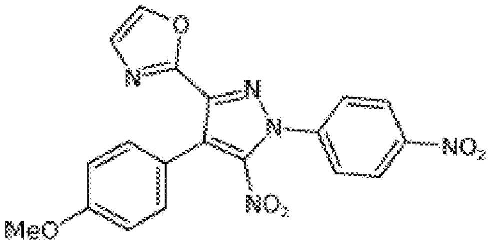
Figure 14:
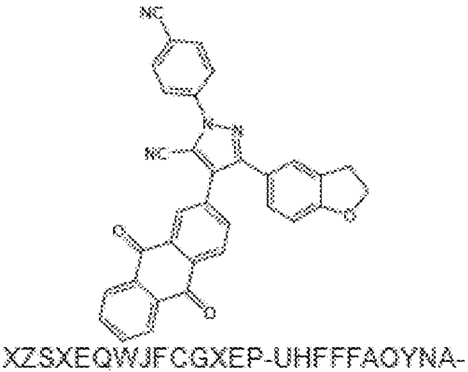
Figure 14:
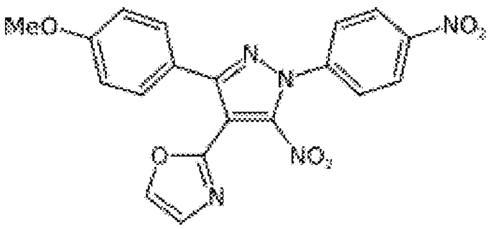
Figure 14:
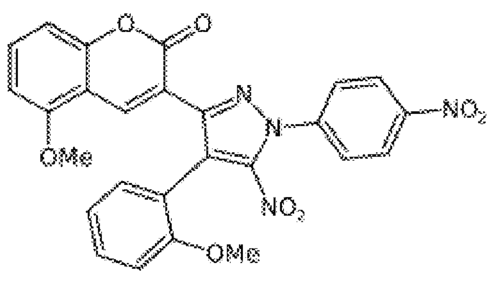
Figure 14:
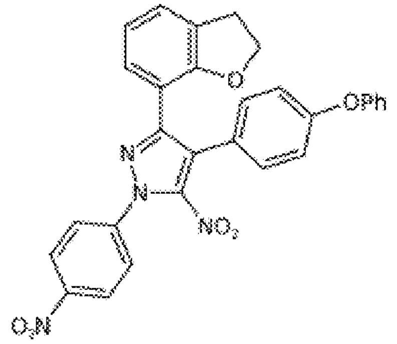
Figure 15:
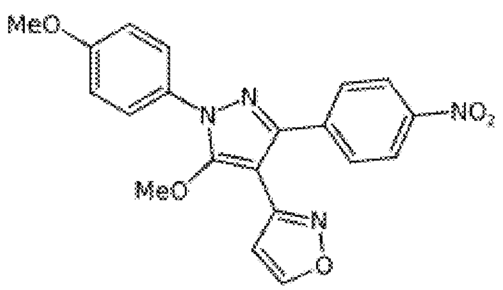
Figure 15:
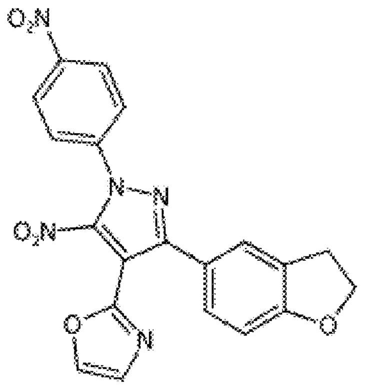
Figure 15:
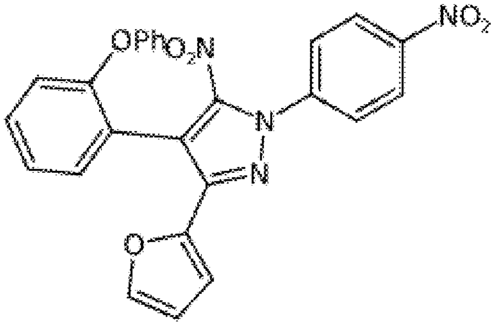
Figure 15:
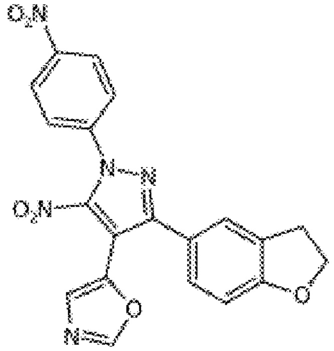
Figure 15:
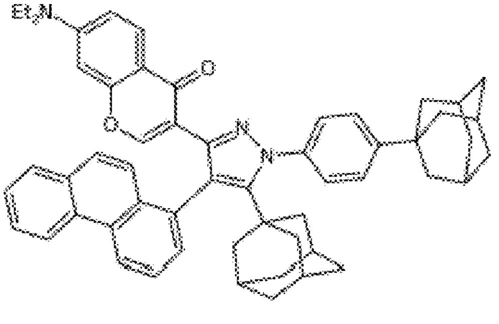
Figure 15:
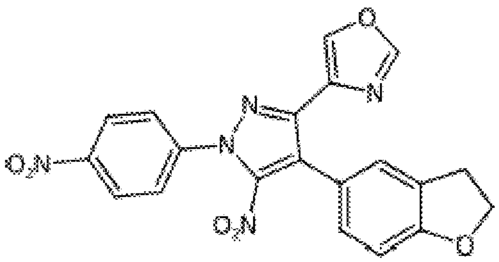
Figure 15:
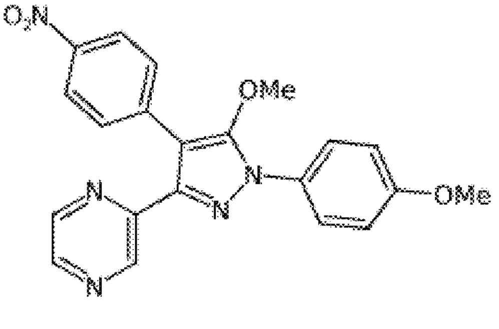
Figure 15:
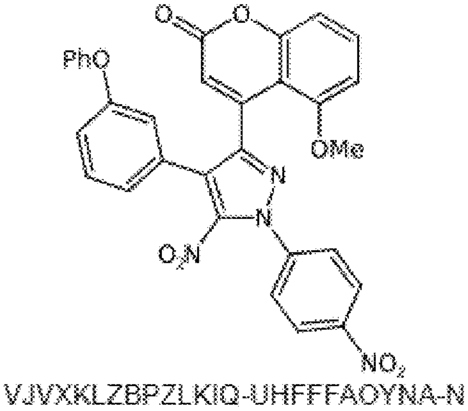
Figure 16:
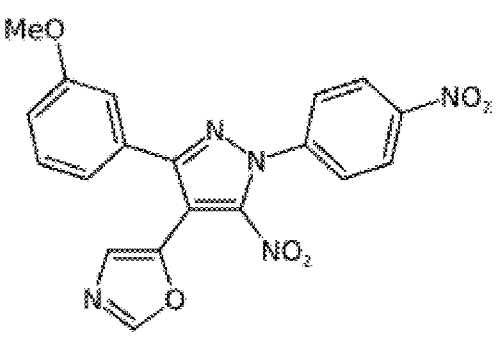
Figure 16:
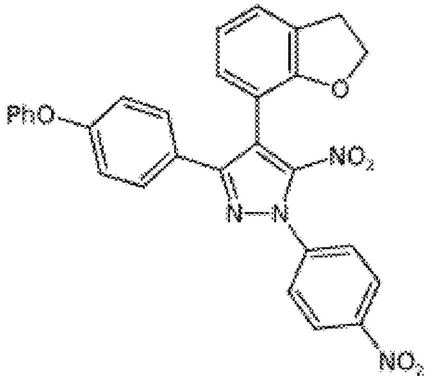
Figure 16:
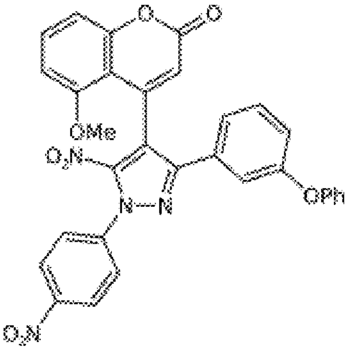
Figure 16:
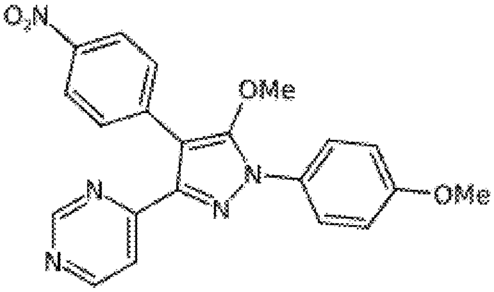
Figure 16:
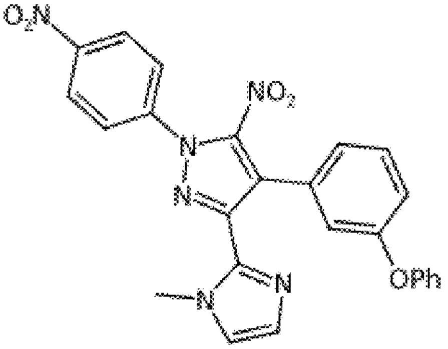
Figure 16:
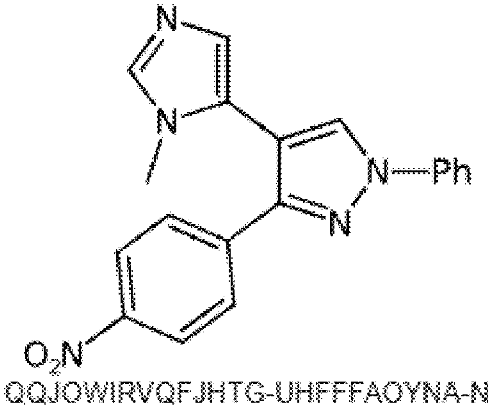
Figure 16:
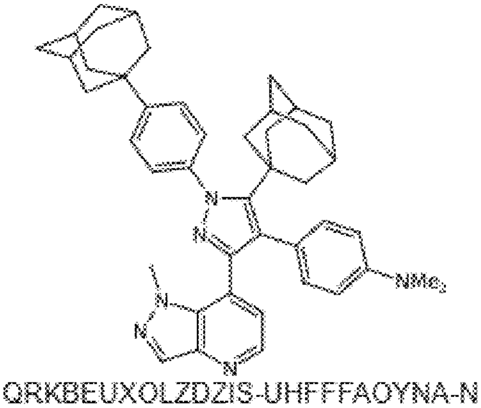
Figure 16:
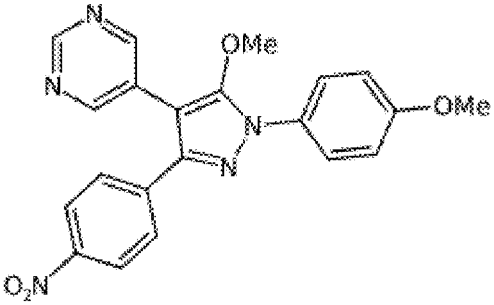
Figure 17:
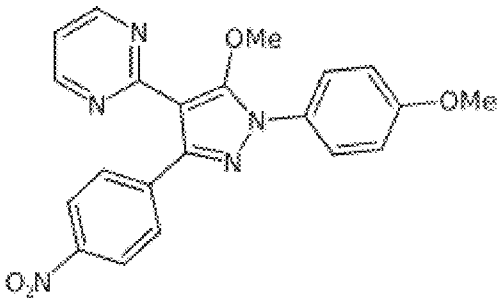
Figure 17:
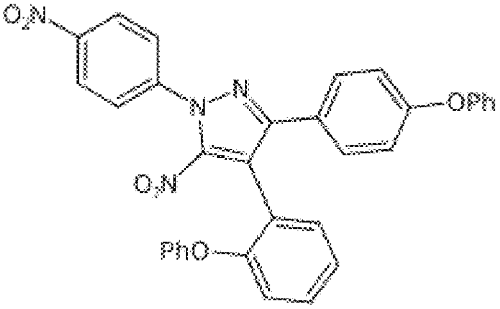
Figure 17:
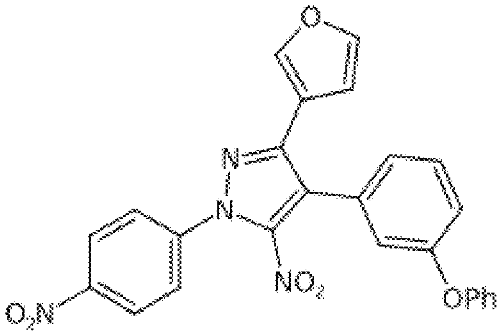
Figure 17:
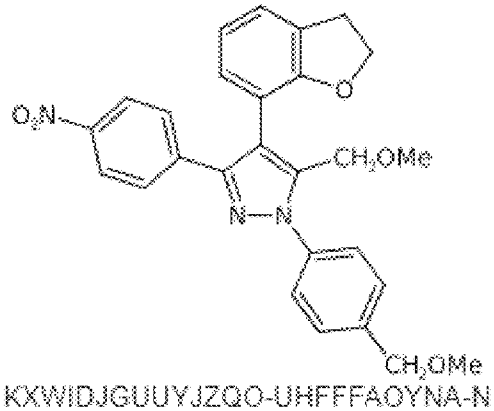
Figure 17:
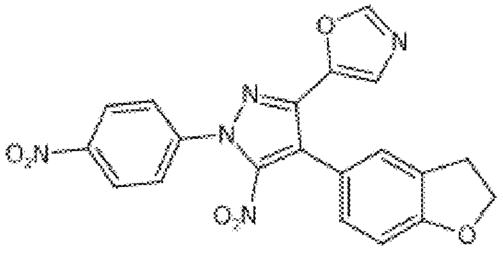
Figure 17:
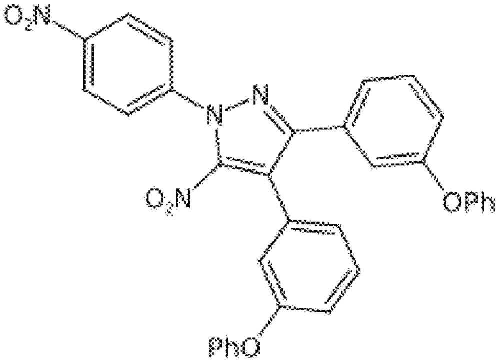
Figure 17:
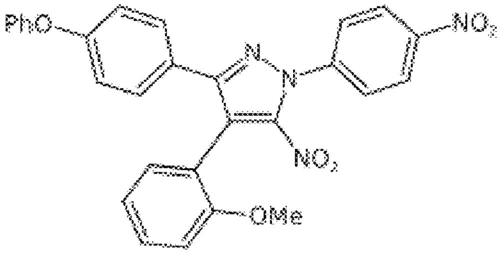
Figure 17:
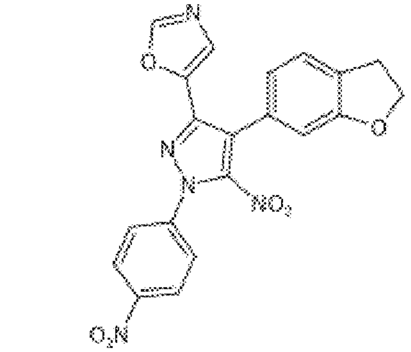
Figure 18:
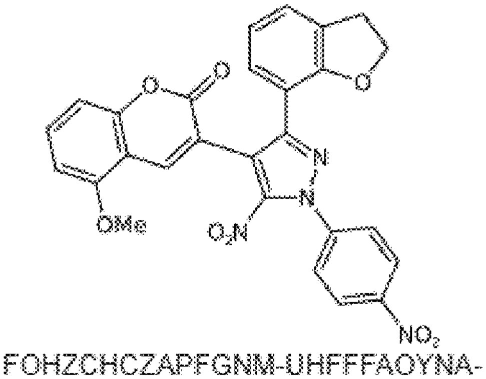
Figure 18:
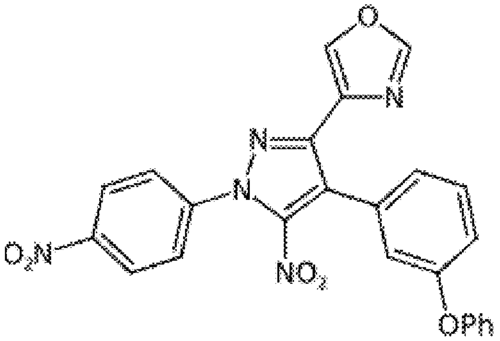
Figure 18:
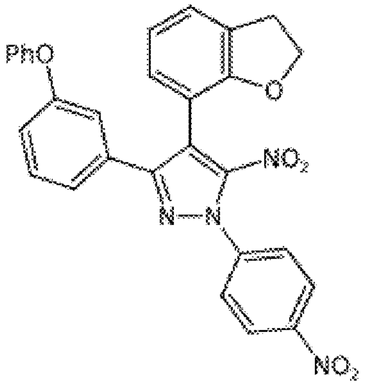
Figure 18:
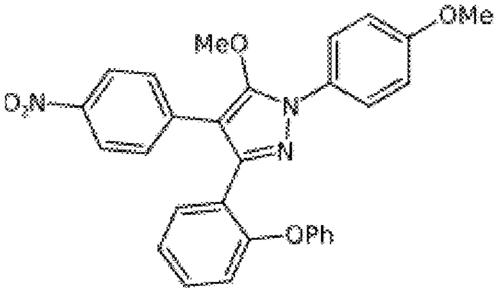
Figure 18:
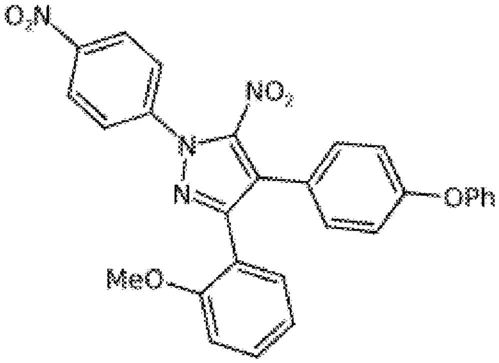
Figure 18:
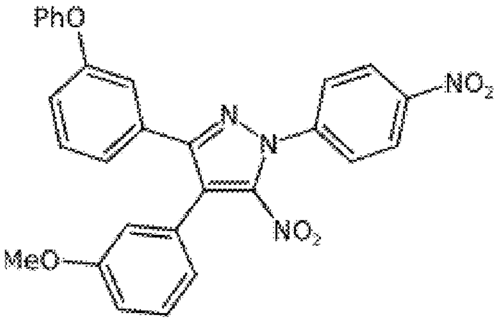
Figure 18:
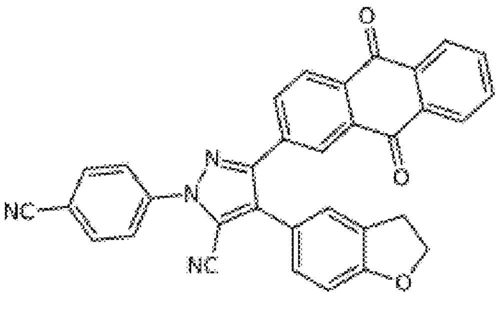
Figure 18:
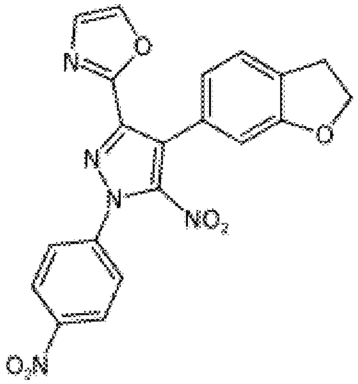
Figure 19:
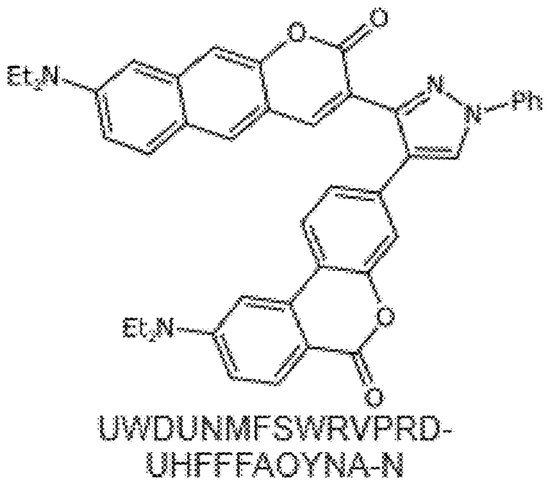
Figure 19:
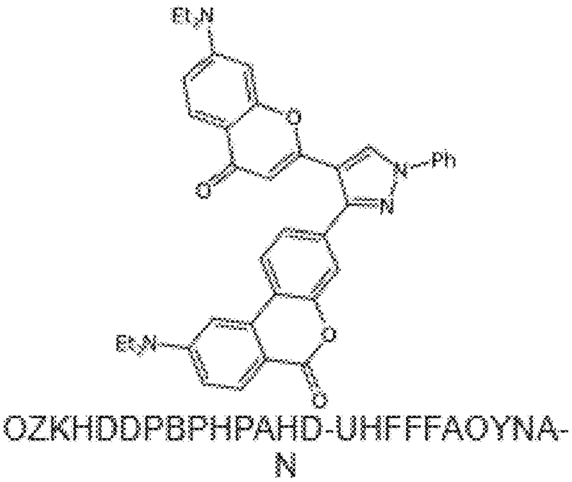
Figure 19:
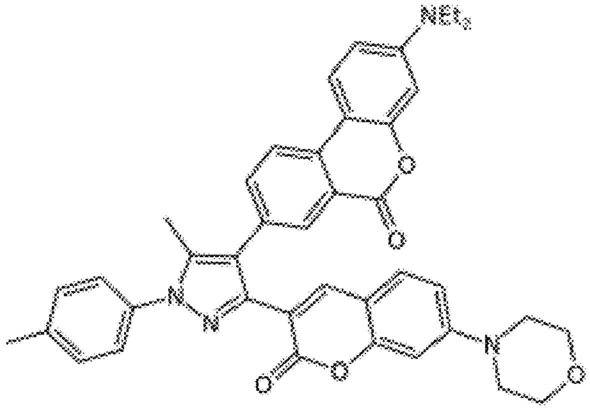

FIG. 6 shows a TD-DFT generated UV-Vis absorption spectrum for Compound 1. This plot was generated by broadening TD-DFT excitation energies with Cauchy distributions with heights proportional to the excitation's oscillator strength. The dotted vertical lines indicate the location of the TD-DFT energy of the five lowest excited states.

The most important excited states ae the lowest few excited states; typically OLED molecules electroluminescence from their lowest energy excited state, which TD-DFT predicts has an absorbance wavelength of 440 nanometers (nm). The difference between the lowest energy absorbance and the lowest energy emission is the Stokes shift for the S1 excited state. As the Stokes shift is rarely negative, the lowest energy absorbance wavelength is therefore an estimate for the upper bound of the wavelength of the molecule's electroluminescent emission. This TD-DFT calculation therefore showed that Compound 1 has the potential to electroluminescence in the blue to green range of visible light.

While several embodiments of the present disclosure have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present disclosure. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present disclosure is/are used. Those skilled in the art will recognize, or be able to ascertain using no more than routine experimentation, many equivalents to the specific embodiments of the disclosure described herein. It is, therefore, to be understood that the foregoing embodiments are presented by way of example only and that, within the scope of the appended claims and equivalents thereto, the disclosure may be practiced otherwise than as specifically described and claimed. The present disclosure is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present disclosure.

In cases where the present specification and a document incorporated by reference include conflicting and/or inconsistent disclosure, the present specification shall control. If two or more documents incorporated by reference include conflicting and/or inconsistent disclosure with respect to each other, then the document having the later effective date shall control.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising"

can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of."

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

When the word "about" is used herein in reference to a number, it should be understood that still another embodiment of the disclosure includes that number not modified by the presence of the word "about."

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. An electroluminescent device, comprising:

an electroluminescent region comprising a pyrazole; and a voltage source able to apply voltage to the electroluminescent region;

wherein the pyrazole comprises a structure:

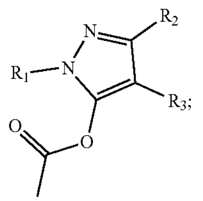

wherein each of $R_1$, $R_2$, and $R_3$ independently comprises a phenyl moiety, or is —H, —OCHO, —$NO_2$, —CN, —$OCH_3$, —$CH_2OCH_3$, —$CH_3$, —OR', —$CH_2OR'$, —R', or —OC(O)R', wherein R' is an alkyl moiety or a phenyl moiety; and wherein $R_1$ comprises a halogen-substituted phenyl moiety and/or $R_2$ comprises a dialkylamine-substituted phenyl moiety and/or $R_3$ comprises an amide-substituted phenyl moiety.

2. The electroluminescent device of claim 1, wherein 2 of $R_1$, $R_2$, and $R_3$ each independently comprises a phenyl moiety.

3. The electroluminescent device of claim 1, wherein each of $R_1$, $R_2$, and $R_3$ independently comprises a phenyl moiety.

4. The electroluminescent device of claim 1, wherein at least two of $R_1$, $R_2$, and $R_3$ are conjugated.

5. The electroluminescent device of claim 1, wherein $R_1$ comprises a halogen-substituted phenyl moiety.

6. The electroluminescent device of claim 5, wherein the halogen is F.

7. The electroluminescent device of claim 1, wherein $R_2$ comprises a dialkylamine-substituted phenyl moiety.

8. The electroluminescent device of claim 1, wherein $R_2$ comprises a dimethylamine-substituted phenyl moiety.

9. The electroluminescent device of claim 1, wherein $R_3$ comprises an amide-substituted phenyl moiety.

10. The electroluminescent device of claim 1, wherein the pyrazole comprises a structure:

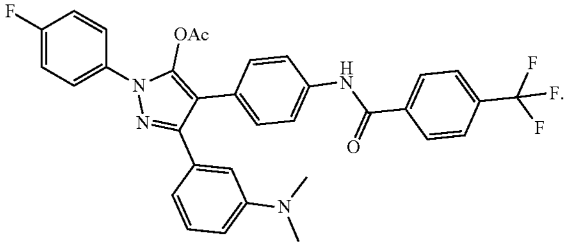 [SMILES: CC(=O)Oc1c(-c2ccc(NC(=O)c3ccc(C(F)(F)F)cc3)cc2)c(-c2cccc(N(C)C)c2)nn1-c1ccc(F)cc1]

11. The electroluminescent device of claim 1, wherein the electroluminescent region exhibits light emission.

12. The electroluminescent device of claim 1, wherein the electroluminescent region exhibits light emission at a wavelength of between 350 nm and 900 nm.

13. A method, comprising:

applying voltage to the electroluminescent device of claim 1 to cause the electroluminescent region to exhibit light emission.

14. An electroluminescent device, comprising:

a cathode;

an anode;

a voltage source electrically connecting the anode and the cathode; and an electroluminescent region comprising a pyrazole, positioned between the cathode and the anode;

wherein the pyrazole comprises a structure:

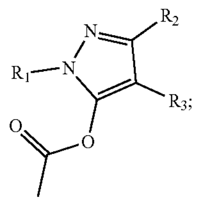

wherein each of $R_1$, $R_2$, and $R_3$ independently comprises a phenyl moiety, or is —H, —OCHO, —$NO_2$, —CN, —$OCH_3$, —$CH_2OCH_3$, —$CH_3$, —OR', —$CH_2OR'$, —R', or —OC(O)R', wherein R' is an alkyl moiety or a phenyl moiety; and wherein $R_1$ comprises a halogen-substituted phenyl moiety and/or $R_2$ comprises a dialkylamine-substituted phenyl moiety and/or $R_3$ comprises an amide-substituted phenyl moiety.

15. The electroluminescent device of claim 14, wherein $R_1$ comprises a halogen-substituted phenyl moiety.

16. The electroluminescent device of claim 14, wherein $R_2$ comprises a dialkylamine-substituted phenyl moiety.

17. The electroluminescent device of claim 14, wherein $R_2$ comprises a dimethylamine-substituted phenyl moiety.

18. The electroluminescent device of claim 14, wherein $R_3$ comprises an amide-substituted phenyl moiety.

19. A method, comprising:

applying voltage to the electroluminescent device of claim 14 to cause the electroluminescent region to exhibit light emission.

* * * * *